United States Patent
Keller et al.

(10) Patent No.: US 7,407,763 B2
(45) Date of Patent: Aug. 5, 2008

(54) SYSTEMS AND METHODS FOR DETECTING AND REGULATING METASTASIS

(75) Inventors: Evan T. Keller, Ann Arbor, MI (US); Zheng Fu, Rochester, MN (US)

(73) Assignee: The Regents of the University of Michigan, Ann Arbor, MI (US)

( * ) Notice: Subject to any disclaimer, the term of this patent is extended or adjusted under 35 U.S.C. 154(b) by 48 days.

(21) Appl. No.: 11/052,444

(22) Filed: Feb. 7, 2005

(65) Prior Publication Data

US 2005/0255503 A1 Nov. 17, 2005

Related U.S. Application Data

(60) Provisional application No. 60/542,374, filed on Feb. 6, 2004.

(51) Int. Cl.
*G01N 33/53* (2006.01)
(52) U.S. Cl. ...................................................... 435/7.1
(58) Field of Classification Search .................. 435/7.1
See application file for complete search history.

(56) References Cited

OTHER PUBLICATIONS

Fu et al (Journal of the National Cancer Institute, Jun. 18, 2003, 95(12): 878-889).*
Fu et al (Proceedings of the American Association for Cancer Research Annual Meeting, Mar. 2002, 43:674-675).*
Fu et al (Journal of the National Cancer Institute, Jun. 18, 2003, 95(12):878-889).*
Tockman et al (Cancer Res., 1992, 52:2711s-2718s).*
Fu et al (proceedings of the American Association for Cancer Research Annual Meeting, Mar. 2002, 43:674-675).*
Vallee et al., Eur. J. Biochem. 268:5831 (2001).
Yeung et al., Nature 401:173 (1999).
Banfield et al., Structure 6:1245 (1998).
Simister et al., Acta Crystallogr. D Biol. Crystallogr. 58:1077 (2002).
Schoentgen et al., FEBS Lett. 369:22 (1995).
Frayne et al., Mol. Reprod. Dev. 49:454 (1998).
Fu et al., J. Natl. Cancer Inst. 95:878 (2003).
Jones et al. Biochim. Biophys. Acta. 1080:78 (1991).
Perry et al., Biochem. J. 301:235 (1994).
Saunders et al., Cell Endocrinol 107:221 (1995).
Frayne et al., Cell Tissue Res. 298:415 (1999).
Taiji et al., J. Neurosci Res. 45:202 (1996).
Bucqoy et al. Eur. J. Biochem. 225:1203 (1994).
Grandy et al., Mol. Endocrinol. 4:1370 (1990).
Robinson et al., Mol. Gen. Genet. 230:241 (1991).
Schoentgen et al., Protein Eng. 5:295 (1992).
Kroslak et al., J. Biol. Chem. 276:39722 (2001).
Yeung et al., Mol. Cell. Biol. 20:3079 (2000).
Corbit et al., J. Biol. Chem. 278 (15):13061 (2003).
Bazzi et al., Biochemistry 31:1125 (1992).
Lorenz et al., Nature 426:574 (2003).
Kaufmann et al., Trends Cell. Biol. 11:526 (2001).
Cory et al., Oncogene 22:8590 (2003).
Yeung et al., Mol. Cell. Biol. 21:7207 (2001).
Yoshida et al., J. Natl. Cancer Inst. 92:1717 (2000).
Dong et al., Cancer Res. 56:4387 (1996).
Yang et al., Cancer Lett. 119:149 (1997).
Steeg et al., J. Natl. Cancer Inst. 80:200 (1988).

* cited by examiner

*Primary Examiner*—Misook Yu
*Assistant Examiner*—Sean Aeder
(74) *Attorney, Agent, or Firm*—Casimir Jones S.C.

(57) ABSTRACT

The present invention relates to compositions and methods for cancer diagnostics and therapeutics, including but not limited to, RKIP cancer markers and RKIP pathway modulators. In particular, the present invention provides compositions and methods of using RKIP in the diagnosis and treatment of prostate cancers.

5 Claims, 14 Drawing Sheets

A

B

Months after surgery

| | All (n=79) | | | |
|---|---|---|---|---|
| | 5 yrs | | 7 yrs | |
| | survival rate (95% CI) | Number at risk | survival rate (95% CI) | Number at risk |
| RKIP+ | 0.87 (0.76, 0.98) | 27 | 0.87 (0.76, 0.98) | 27 |
| RKIP- | 0.57 (0.43, 0.77) | 18 | 0.52 (0.36, 0.74) | 10 |

| Models | | HR (95%CI) | P value |
|---|---|---|---|
| Univariate | RKIP | 0.208 (0.068-0.634) | 0.0058 |
| Multivariable | RKIP | 0.159 (0.045-0.560) | 0.0042 |
| | Tumor size | 1.328 (0.457-3.858) | 0.6027 |
| | Pathological stage | 1.159 (0.320-4.195) | 0.8221 |
| | SM | 7.682 (2.316-25.47) | 0.0009 |
| | DRE | 1.386 (0.402-4.781) | 0.6050 |
| | Ln[PSA] | 2.508 (1.074-5.858) | 0.0337 |
| | Gland weight | 1.006 (0.966-1.048) | 0.7747 |

Months after surgery

| | Gleason=6+7 (n=73) | | | |
|---|---|---|---|---|
| | 5 yrs | | 7 yrs | |
| | survival rate (95% CI) | Number at risk | survival rate (95% CI) | Number at risk |
| RKIP+ | 0.88 (0.77,1.00) | 24 | 0.88 (0.77,1.00) | 24 |
| RKIP- | 0.61 (0.46, 0.80) | 18 | 0.55 (0.38, 0.77) | 10 |

SYSTEMS AND METHODS FOR DETECTING AND REGULATING METASTASIS

This application claims priority to U.S. Provisional Application Ser. No. 60/542,374, filed Feb. 6, 2004, which is hereby incorporated by reference in its entirety.

This application was supported in part by NIH grants RR07008 and CA069568. The government may have certain rights in the invention.

FIELD OF THE INVENTION

The present invention relates to compositions and methods for cancer diagnostics and therapeutics, including but not limited to, RKIP cancer markers and RKIP pathway modulators. In particular, the present invention provides compositions and methods of using RKIP in the diagnosis and treatment of prostate cancers.

BACKGROUND OF THE INVENTION

Most forms of cancer do not have diagnostic screening tests available or sufficient therapeutic interventions. For the cancers that do have screening tests available, the tests are frequently invasive, expensive, and lack strong diagnostic utility. Many current therapies, while improving, permit recurrence and metastasis.

For example, afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer in 2001 and 39,200 will die.

Prostate cancer is typically diagnosed with a digital rectal exam and/or prostate specific antigen (PSA) screening. An elevated PSA level can indicate the presence of PCA. PSA is used as a marker for prostate cancer because it is essentially restricted to prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

The advent of prostate specific antigen (PSA) screening has led to earlier detection of PCA and significantly reduced PCA-associated fatalities. Elevated serum PSA levels, however, are often detected in patients with non-malignant conditions such as benign prostatic hyperplasia (BPH), and provide little information about the aggressiveness of the cancer detected.

In addition, colon cancer, which is the second most frequently diagnosed malignancy in the United States as well as the second most common cause of cancer death, lacks an effective screening assay. The prognosis of colon cancer is clearly related to the degree of penetration of the tumor through the bowel wall and the presence or absence of nodal involvement, thus making early diagnosis very important for long-term survival.

A fecal occult blood test (FOBT) is a test used to check for hidden blood in the stool. Sometimes cancers or polyps can bleed, and FOBT is used to detect small amounts of bleeding. In addition, screening tests (such as a rectal examination, proctoscopy, and colonoscopy) may be done regularly in patients who are at high risk of colon cancer or who have a positive FOBT result. The proctoscopy examination finds about half of all colon and rectal cancers. After treatment, a blood test (to measure amounts of carcinoembryonic antigen or CEA in the blood) and x-rays may be done to screen for recurrence. CEA is a serum glycoprotein frequently used in the management of patients with colon cancer. However, a review of the use of this tumor marker suggests that CEA is not a valuable screening test for colorectal cancer due to the large numbers of false-positive and false-negative reports.

Thus, development of additional serum and tissue biomarkers specific to cancer such and prostate are needed to supplement the currently available screening methods. In particular, biological markers that characterize the stage of cancer are needed. The art is also in need of new biological targets for controlling the spread of cancer.

SUMMARY OF THE INVENTION

The present invention relates to compositions and methods for cancer diagnostics and therapeutics, including but not limited to, RKIP cancer markers and RKIP pathway modulators. In particular, the present invention provides compositions and methods of using RKIP in the diagnosis and treatment of prostate or breast cancers.

Accordingly, in some embodiments, the present invention provides a method for characterizing cancer, comprising the steps of providing a sample from a subject diagnosed with cancer; and detecting the presence, absence or amount of expression of RKIP in the sample. In some embodiments, the absence of the RKIP expression in the sample is indicative of metastatic cancer in the subject. In other embodiments, the absence of the RKIP expression in the sample is indicative of cancer likely to metastasize in the subject. In some embodiments, the cancer is prostate cancer. In other embodiments, the cancer is breast cancer. In some embodiments, the sample is a tumor sample. In other embodiments, the sample is a tissue sample (e.g., prostate or breast tissue). In still further embodiments, the sample is selected from the group consisting of serum, plasma, blood, and urine. In certain embodiments, detecting the presence or absence of RKIP comprises detecting the presence or absence of RKIP mRNA. In some embodiments, detecting the presence or absence of RKIP mRNA comprises exposing the sample to a nucleic acid probe complementary to at least a portion of the RKIP mRNA. In other embodiments, detecting the presence of RKIP mRNA comprises a detection assay selected from the group consisting of a Northern blot, in situ hybridization, reverse-transcriptase polymerase chain reaction, and microarray analysis. In certain further embodiments, detecting the presence or absence of RKIP comprises detecting the presence or absence of an RKIP polypeptide. In some embodiments, detecting the presence of a RKIP polypeptide comprises exposing the RKIP polypeptide to an antibody that specifically binds to RKIP and detecting the binding of the antibody to the RKIP polypeptide. In some embodiments, the method further comprises step c) providing a prognosis to the subject. In still further embodiments, the method further comprises the step of d) administering a metastasis regulating agent to the subject. In some embodiments, the metastasis regulating agent is a compound that increases expression of RKIP in the subject. In other embodiments, the metastasis regulating agent is a compound that increases the amount of RKIP polypeptide in the subject. In still further embodiments, the metastasis regulating agent is a compound that reduces activity or expression of a molecule that is upregulated in the absence of RKIP (e.g., ERK, RAF, or MAPK). In some embodiments, the compound is produced in a cell that is transplanted into the subject. In certain embodiments, the subject is an animal and the method is conducted for research purposes (e.g., drug screening or drug trials).

In other preferred embodiments, the method further comprises the step of administering an agent that increases RKIP expression. In preferred embodiments, the agent is an androgen receptor ligand. In yet other preferred embodiments, the androgen receptor ligand is dihydrotestosterone.

In other embodiments, the present invention provides a kit for characterizing and/or treating cancer in a subject, comprising a reagent that specifically detects the presence of absence of expression of RKIP; and instructions for using the kit for characterizing cancer in the subject. In some embodiments, the reagent comprises an antibody that specifically binds to RKIP. In other embodiments, the reagent comprises a nucleic acid probe that specifically binds to a RKIP mRNA. In some embodiments, the instructions comprise instructions required by the United States Food and Drug Administration for use in in vitro diagnostic products.

In still further embodiments, the present invention provides a method of screening compounds, comprising providing a cell sample comprising cells lacking endogenous RKIP expression; and one or more test compounds; and contacting the sample with the test compound; and detecting a change in RKIP signaling in the sample in the presence of the test compound relative to the absence of the test compound. In some embodiments, contacting the sample with the test compound results in restoration of RKIP signaling in the cell sample. In some embodiments, the cells are metastatic cancer cells (e.g., metastatic prostate or breast cancer cells). In some embodiments, contacting the sample with the test compound results in death of the cells. In other embodiments, contacting the sample with the test compound results in impaired proliferation of the cells. In some embodiments, the cell is in vitro. In other embodiments, the cell is in vivo. In some embodiments, the test compound comprises a drug.

In yet other embodiments, the present invention provides a method of regulating metastasis in an animal comprising administering an effective amount of a metastasis regulating compound. In some embodiments, the metastasis regulating agent is a compound that increases expression of RKIP in the subject. In other embodiments, the metastasis regulating agent is a compound that increases the amount of RKIP polypeptide in the subject. In still further embodiments, the metastasis regulating agent is a compound that reduces activity or expression of a molecule that is upregulated in the absence of RKIP (e.g., ERK, RAF, or MAPK). In some embodiments, the compound is produced in a cell that is transplanted into the subject. In certain embodiments, the subject is an animal and the method is conducted for research purposes (e.g., drug screening or drug trials).

GENERAL DESCRIPTION OF THE INVENTION

Figure 1:
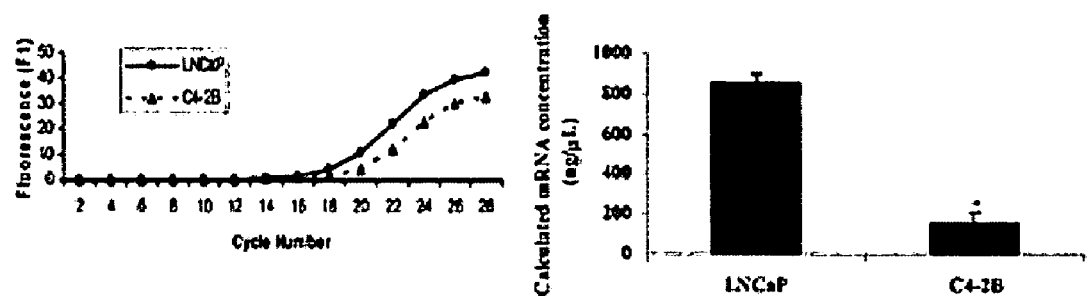
FIG. 1 presents differential expression of raf kinase inhibitor protein (RKIP) in prostate cancer cells. A) Quantitative analysis of RKIP expression in LNCaP vs C4-2B cells. Light-Cycler fluorescence detection of RKIP of LNCaP (-●-), C4-2B (-▲-) mRNA by RT-PCR of total RNA from LNCaP and C4-2B cells. B) Immunoblot analysis of RKIP expression in LNCaP and C4-2B cells.
Figure 1:
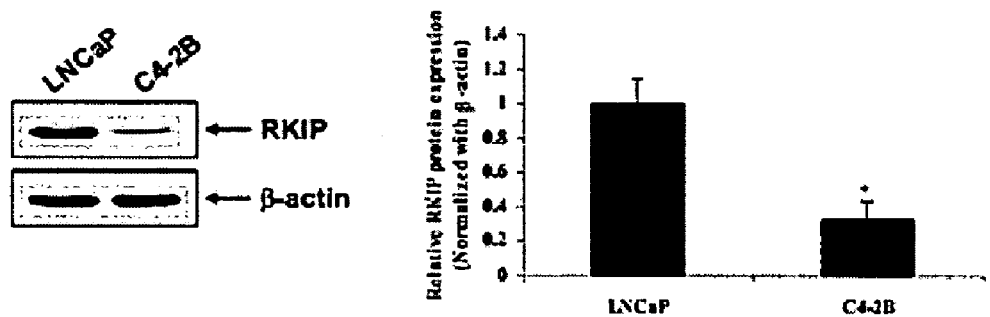

Raf kinase inhibitor protein (RKIP), a member of the phosphatidyl ethanolamine binding protein (PEBP) family, is a small, cytosolic protein originally purified from bovine brain (Vallee et al., Eur. J. Biochem. 268:5831 (2001); Yeung et al., Nature 401:173 (1999)). The RKIP family of proteins is highly conserved and does not share significant homology with any other protein family (Banfield et al., Structure 6:1245 (1998)). RKIP was initially identified as human PEBP where it was shown to have a role in lipid metabolism and phospholipid membrane biogenesis. Recent investigations have identified that RKIP inhibits Raf-mediated activation of MEK, which accounts for it current name. Aberrant RKIP activity is associated with an increasing number of diseases via its association with signal transduction pathways (Yeung et al., supra; Banfield et al., supra).

RKIP is synthesized locally in many tissues where it has been shown to be present in the cytoplasm and at the plasma membrane as determined by immunohistochemical staining (Simister et al., Acta Crystallogr. D Biol. Crystallogr. 58:1077 (2002)). While RKIP homologues can be found in testicular and epididymal luminal secretions, it is not found in blood, saliva, milk, uterine fluid, parotid fluid, prostate secretions, or seminal vesicle secretions (Schoentgen et al., FEBS Lett. 369:22 (1995)).

Rat RKIP expression has been found in oligodendrocytes and Schwann cells of the neuronal tissue; spermatids, Leydig cells, and epididymal epithelium of the testis; steroidogenic cells of the adrenal gland zona fasciculata; proximal kidney tubule epithelium; enterocytes, goblet cells, and plasma cells of the small intestine; plasma cells of the lymph node; plasma cells and megakaryocytes of the spleen; heart; liver; and epididymis (Frayne et al., Mol. Reprod. Dev. 49:454 (1998)). Some expression has also been found in bronchioles of the lung, mesenteric lymph node, oviduct, ovary, lactating mammary glands, uterus, and thyroid. RKIP expression has also been found in normal tissue and nonmetastatic prostate cancer cells, but is expressed weakly in metastatic prostate cancer cells (See e.g., Fu et al., J. Natl. Cancer Inst. 95:878 (2003); herein incorporated by reference and the Experimental Section below).

RKIP appears to have a variety of functions depending on the tissue in which it is localized. Several lines of evidence suggest that it is involved with mammalian spermatogenesis and male fertility (Jones et al. Biochim. Biophys. Acta. 1080:78 (1991); Perry et al., Biochem. J. 301:235 (1994); Saunders et al., Cell Endocrinol 107:221 (1995)).

Although RKIP is expressed in multiple tissues of the rat, higher expression levels can be found in the testis, brain oligodendricytes, Schwann cells, Purkinje cells of the cerebellum and within cortical and hippocampal layers of the brain (Frayne et al., Cell Tissue Res. 298:415 (1999)). In rat medial septal nuclei, RKIP was found to enhance in vitro acetylcholine synthesis by upregulating choline acetyltransferase and possibly stimulating cholinergic neuronal pathways (Taiji et al., J. Neurosci Res. 45:202 (1996)).

RKIP interacts with small GTP-binding proteins, but not GTP itself (Bucqoy et al. Eur. J. Biochem. 225:1203 (1994)) and can be purified along with µ opioid receptors via morphine affinity chromatography using tissue derived from rat brain (Grandy et al., Mol. Endocrinol. 4:1370 (1990)). Using hydrophobic cluster analysis and molecular modeling, Schoentgen et al. showed that the bovine RKIP may possess a potential nucleotide binding site and suggested that it may belong to the kinase family and promote the transfer of hydrophobic ligands to the plasma membrane (Robinson et al., Mol. Gen. Genet. 230:241 (1991); Schoentgen et al., Protein Eng. 5:295 (1992)). Co-expression of human RKIP with human opioid or somatastatin receptors (G-protein-coupled receptors) in *Xenopus laevis* oocytes provided in vivo evidence that RKIP could modulate G-protein-coupled signaling (Kroslak et al., J. Biol. Chem. 276:39772 (2001)).

The role of RKIP in cell signaling was identified in a yeast two-hybrid assay for screening clones from a human T-cell library that bound to Raf-1 kinase binding domains (Yeung et al., supra). RKIP was shown to bind Raf-1, MEK-1 and weakly bind to ERK-2, interfering with MEK phosphorylation and activation by Raf-1. However, RKIP was not a substrate for Raf-1 or MEK. RKIP did not bind to Ras, nor possess kinase activity. It appears that RKIP acts to set the threshold for Raf-1 activation and subsequent activation of the MEK/ERK pathway. Raf-1 dissociates from its complex with MEK in the presence of RKIP. As a result, downstream mitogen-activated protein kinase (MAPK) signaling is interrupted and diminished. As stated earlier, RKIP can bind to Raf-1 or MEK, yet not at the same time, and binding to either one is enough to cause downstream inhibition (Keung et al., Mol. Cell. Biol. 20:3079 (2000)).

Protein kinase C (PKC), which phosphorylates target proteins that control growth, differentiation and transcription, can inactivate RKIP through phosphorylation of RKIP on serine 153 and alleviate its inhibition of Raf-1 (Corbit et al., J. Biol. Chem. M210015200 (2003)). PKC is normally recruited to the plasma membrane and activated by diacylglycerol. Its location near the plasma membrane may place it in close proximity to RKIP, which also binds to phospholipids (Bazzi et al., Biochemistry 31:1125 (1992)). As a result, PKC along with RKIP, function as unique selective regulators of the Raf-1/MEK/ERK growth factor signaling cascade. When RKIP is phosphorylated, it releases from Raf-1 and can bind onto G-protein-coupled receptor kinase-2 (GRK-2) preventing GRK-2's ability to inhibit G-protein-coupled receptor activity (Lorenz et al., Nature 426:574 (2003)).

Apoptosis is a physiological cell self-destruction program that has been implicated in multiple biological and pathological processes including cancer. Besides the inappropriate expression of tumor promoting genes and the silencing of tumor suppressor genes the acquisition of resistance toward apoptosis is perhaps the next important landmark in malignant tumor development. Therefore, understanding the underlying mechanisms of apoptosis is of importance in determining the efficacy of cancer treatments. In drug-curable malignancies, apoptosis is a prominent mechanism associated with the induction of tumor remission. Further, the expression of apoptosis modulators within a tumor appears to correlate with its sensitivity to traditional therapies. In mammals, the signaling pathways leading to apoptosis converge on activation of either caspase-8 or -9 (Kaufmann et al., Trends Cell. Biol. 11:526 (2001)).

Cancer cells can acquire resistance to apoptosis by various mechanisms. It can involve regulators of various apoptosis signaling pathways. For example, cancer cells can acquire resistance by up-regulating the anti-apoptotic molecules BCL2 or down-regulating the expression of pro-apoptotic molecule BAX (Cory et al., Oncogene 22:8590 (2003)). It can also involve pro-survival signaling pathways that impinge on apoptosis signaling. Pro-survival signaling pathways that are parts of cell failsafe mechanism against transformation include the PI3/AKT, Raf and NF-κB. Experiments conducted during the course of development of the present invention demonstrated that down-regulating the expression of RKIP is another mechanism cancer cell employed to evade apoptosis.

RKIP also antagonizes the signal transduction pathways that mediate the activation of the transcription factor NF-κB in response to TNF-α and interleukin 1 beta (IL-1β) stimulation (Keung et al., Mol. Cell. Biol. 21:7202 (2001)). Modulation of RKIP expression levels affected NF-κB signaling independently of the MAPK pathway.

Genetic epistasis analysis involving the ectopic expression of kinases acting in the NF-κB pathway indicated that RKIP acts upstream of the kinase complex that mediates the phosphorylation and inactivation of the inhibitor of NF-κB (IκB). In vitro kinase assays showed that RKIP antagonizes the activation of IκB kinase (IKK) activity elicited by TNF-α. RKIP physically interacted with four kinases of the NF-κB activation pathway, NF-κB inducing kinase (NIK), transforming growth factor beta (TGF-β) activated kinase (TAK1), IKKα and IKKβ. This mode of action is similar to the interaction of RKIP with Raf-1 and MEK1 in the MAPK pathway.

Experiments conducted during the course of development of the present invention demonstrated that RKIP can induce apoptosis in certain prostate and breast carcinoma cell lines. The effect of RKIP on apoptosis signaling pathway is specific to cancer cells.

Further experiments conducted during the course of development of the present invention demonstrated that RKIP induces apoptosis by modulating the activities of Raf and NF-kB. The present invention is not limited to a particular mechanism. Indeed, an understanding of the mechanism is not necessary to practice the present invention. Nonetheless, it is contemplated that these data implicate that RKIP can modulate cancer cell resistance to chemotherapy. It is contemplated that loss of RKIP has an overall anti-apoptotic effect.

Metastasis is defined as the formation of progressively growing secondary tumor foci at sites discontinuous from the primary lesion. The metastatic process is a multi-step mechanism in which a metastatic cancer cell escapes from the primary tumor, enters the circulation, invades a distant tissue site and grows into a macroscopic tumor at the target site. Since many steps are required for metastasis to occur, it is possible to block metastasis by inhibiting a single gene that is required for the completion of any one of these steps. Several studies have shown that the loss of function of specific genes called metastasis suppressor genes (MSG) is an important event in the progression to malignancy (Yoshida et al., J. Natl. Cancer Inst. 92:1717 (2000); Dong et al., Cancer Res. 56:4387 (1996); Yang et al., Cancer Lett. 119:149 (1997); Steeg et al., J. Natl. Cancer Inst. 80:200 (1998)). Due to their ability to regulate the metastatic process, MSG are potential diagnostic and therapeutic targets.

Experiments conducted during the course of development of the present invention examined the difference in gene expression between a non-metastatic prostate cancer cell line and a metastatic prostate cancer cell line. RNA expression of several genes was altered between these two lines. RKIP was one a few genes found to be expressed at a lower level in the metastatic compared to the non-metastatic cell line. The present invention is not limited to a particular mechanism. Indeed, an understanding of the mechanism is not necessary to understand the present invention. Nonetheless, it is contemplated that that loss of RKIP is associated with the development of metastasis.

Further experiments examined RKIP protein expression in non-neoplastic prostate tissue, primary prostate cancer and prostate cancer metastases. RKIP expression level was highest for benign tissue, lower for cancerous tissue (declining with increasing Gleason score), and absent in metastases ($P<0.001$, Mantel-Haneszel chi-square test). These results show that loss of RKIP is associated with the development of prostate cancer metastases. Additional experiments conducted during the course of development of the present invention demonstrated that increased RKIP expression is associated with decreased recurrence of prostate cancer.

To examine the function of RKIP during prostate cancer progression, RKIP expression was modulated in prostate cancer cells to determine the effect of different RKIP levels on the prostate cancer cells metastatic ability. Modulating RKIP expression had no effect on the ability of the cells to grow in vitro or on their ability to form colonies in soft agar. These results show that modulation of RKIP expression has no effect on these two primary tumorigenic properties of human prostate cancer cells. However, to examine whether changes of RKIP expression are associated with cancer cell invasiveness, the effect of modulating RKIP expression on the in vitro invasive ability of the prostate cancer cells was examined. Increasing RKIP expression in metastatic cancer cells decreased invasive ability. Decreasing RKIP expression, using antisense, in non-metastatic prostate cancer cells increased invasive ability. The present invention is not limited to a particular mechanism. Indeed, an understanding of the mechanism is not necessary to understand the present invention. Nonetheless, it is contemplated that these results show that RKIP expression is inversely associated with the invasiveness of prostate cancer cells.

To determine if the in vitro results had relevance to in vivo metastasis, experiments were conducted to determine if increasing RKIP expression decreased metastasis in a murine model. Either (1) metastatic prostate cancer cells transfected with empty vector so they expressed low basal levels of RKIP or (2) the same prostate cancer cells that were engineered to express increased levels of RKIP were implanted into mouse prostates. Tumor growth at the injection site in the prostates was identical between both groups. In contrast, increasing RKIP expression in the tumor cells resulted in decreasing the number of mice that developed lung metastases by 70%. Furthermore, in the mice that had received cells expressing increased RKIP and that developed metastases, the number of metastases was far fewer than in the mice that had received the cells expressing low levels of RKIP. Additionally, there was less vascular formation and less vascular invasion in the primary tumors derived from the mice that received the cells engineered to express RKIP. The present invention is not limited to a particular mechanism. Indeed, an understanding of the mechanism is not necessary to understand the present invention. Nonetheless, it is contemplated taken together, these results show that RKIP functions as a suppressor of metastasis through decreasing angiogenesis and vascular invasion.

Accordingly, in some embodiments, the present invention provides methods of diagnosing, studying and treating cancer comprising altering RKIP expression and/or signaling in cancer cells.

DEFINITIONS

To facilitate an understanding of the present invention, a number of terms and phrases are defined below:

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the terms "epithelial tissue" or "epithelium" refer to the cellular covering of internal and external surfaces of the body, including the lining of vessels and other small cavities. It consists of cells joined by small amounts of cementing substances. Epithelium is classified into types on the basis of the number of layers deep and the shape of the superficial cells.

As used herein, the term "normal epithelium of prostate or colon" refers to prostate or colon epithelium that does not show any detectable indication of cancerous or pre-cancerous conditions.

As used herein, the term "cancerous epithelium of prostate or colon" refers to prostate or colon epithelium that shows a detectable indication of cancerous or pre-cancerous conditions.

As used herein, the term "LNCaP cells" refers to a non-metastatic prostate cancer cell line. As used herein, the term "C4-2B cells" refers to a metastatic cell line derived from LNCaP cells.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass or increased PSA level) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests (e.g., PSA).

As used herein, the term "initial diagnosis" refers to a test result of initial cancer diagnosis that reveals the presence or absence of cancerous cells (e.g., using a biopsy and histology). An initial diagnosis does not include information about the stage of the cancer or the risk of prostate specific antigen failure.

As used herein, the term "prostate tumor tissue" refers to cancerous tissue of the prostate. In some embodiments, the prostate tumor tissue is "post surgical prostate tumor tissue."

As used herein, the term "post surgical tumor tissue" refers to cancerous tissue (e.g., prostate tissue) that has been removed from a subject (e.g., during surgery).

As used herein, the term "identifying the risk of said tumor metastasizing" refers to the relative risk (e.g., the percent chance or a relative score) of a tumor (e.g., prostate tumor tissue) metastasizing.

As used herein, the term "identifying the risk of said tumor recurring" refers to the relative risk (e.g., the percent chance or a relative score) of a tumor (e.g., prostate tumor tissue) recurring in the same organ as the original tumor (e.g., prostate).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer. Cancers may be characterized by the identification of increased or decreased amounts of RKIP in tumor tissues.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of RKIP.

As used herein, the term "reagent(s) capable of specifically detecting RKIP expression" refers to reagents used to detect the expression of RKIP. Examples of suitable reagents include but are not limited to, nucleic acid probes capable of specifically hybridizing to RKIP mRNA or cDNA, and antibodies (e.g., monoclonal antibodies of the present invention).

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

As used herein, the term "non-human transgenic animal lacking a functional RKIP gene" refers to a non-human animal (preferable a mammal, more preferably a mouse) whose endogenous RKIP gene has been inactivated (e.g., as the result of a "RKIP knockout" or a "RKIP knock-in").

As used herein, the terms "RKIP knockout" refers to a non-human animal (e.g., a mouse) lacking a functional RKIP gene. In some embodiments, the entire RKIP gene is deleted. In other embodiments, the gene is inactivated via other means (e.g., deletion of essential portions or inversions of some or all of the RKIP gene). In other embodiments, the RKIP gene is inactivated using antisense inhibition. RKIP knockout include conditional knockouts (e.g., selective inhibition of gene activity). RKIP knockout mice may be made using any suitable method including, but not limited to, those described herein. RKIP genes can also be inactivated via the construction of a "RKIP knock-in" in which the gene is inactivated by the insertion of exogenous DNA into a region of the gene required for function.

As used herein, the term "mimetic" refers to a small molecule compound that mimics the binding of a RKIP to a ligand (e.g., RAF).

As used herein, the term "detecting a decrease in viability" refers to a decrease in the number of living cells in a culture. In preferred embodiments, the decrease is due to the induction of programmed cell death (e.g., apoptosis) in some or all of the cells in a population.

As used herein, the term "induces cell death" refers to a molecule (e.g., a test compound or a drug) that induces a programmed cell death (e.g., apoptosis).

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of form amide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

DETAILED DESCRIPTION OF THE INVENTION

The present invention relates to compositions and methods for cancer diagnostics and therapeutics, including but not limited to, RKIP cancer markers and RKIP pathway modulators. In particular, the present invention provides compositions and methods of using RKIP in the diagnosis and treatment of prostate cancers.

I. RKIP as a Marker for Cancer

In some embodiments, the present invention relates to compositions and methods for cancer diagnostics, including but not limited to, RKIP cancer markers. In particular, the present invention provides markers (e.g., RKIP) whose expression is specifically altered in cancerous tissues (e.g., epithelial tissues such as prostate and colon). Such markers find use in the diagnosis and characterization of cancer.

Experiments conducted during the development of the present invention demonstrated that metastatic prostate cancer cells had decreased expression of RKIP relative to non-metastatic prostate cancer cells. Further experiments conducted during the course of development of the present invention demonstrated that increased RKIP expression is correlated with increased survival in prostate cancer patients. Additional experiments conducted during the course of development of the present invention demonstrated that RKIP tends to be higher in normal tissues than in pre-neoplastic and neoplastic breast and metastases. Tumor emboli are negative. Accordingly, in some embodiments, the present invention provides methods of characterizing cancer (e.g., providing a prognosis) comprising detecting decreased levels of RKIP expression.

In some preferred embodiments of the present invention, RKIP diagnostic assays include a control sample (e.g., a non-metastatic cancer or normal cell sample) to use in the detection of decreased or absent RKIP expression. For example, in embodiments comprising the detection of RKIP expression in tissue (e.g., biopsy) sample, the control is a normal or non-metastatic tissue sample. In embodiments comprising the detection of RKIP expression in blood, urine, or other bodily fluids, the control sample is a bodily fluid sample from a normal individual or an individual with non-metastatic cancer.

In some embodiments, the present invention provides methods for detection of RKIP. In preferred embodiments, the presence of RKIP protein or mRNA is measured directly. In some embodiments, the absence or decrease in RKIP mRNA or protein is detected in tissue samples (e.g., biopsy samples). In other embodiments, an absence or decrease in RKIP mRNA or protein is detected in bodily fluids (e.g., serum, plasma, or urine). The present invention further provides kits for the detection of RKIP. In preferred embodiments, the presence of RKIP is used to provide a diagnosis or prognosis to a subject.

In some preferred embodiments, RKIP protein or a decrease in levels of RKIP protein is detected. Protein expression may be detected by any suitable method. In some embodiments, proteins are detected by binding of an antibody specific for the protein. Any antibody (monoclonal or polyclonal) that specifically detects RKIP may by utilized. Methods for the generation of antibodies are described below.

Antibody binding is detected by techniques known in the art. For example, in some embodiments where RKIP protein is detected in bodily fluids, antibody binding is detected using a suitable technique, including but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays. In other embodiments, where RKIP protein is detected in tissue samples, immunohistochemistry is utilized for the detection of antibody binding.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the presence or absence of a series of proteins corresponding to cancer markers is utilized.

In other embodiments, the immunoassay described in U.S. Pat. Nos. 5,599,677 and 5,672,480, each of which is herein incorporated by reference, is utilized. In other embodiments, proteins are detected by immunohistochemistry.

In other embodiments, RKIP or the decease or absence of RKIP is detected at the level of RKIP RNA. In some embodiments, RKIP RNA is detected by measuring the expression of corresponding mRNA in a tissue sample (e.g., prostate or colon tissue). mRNA expression may be measured by any suitable method, involving, but not limited to, hybridization methods, amplification methods, sequencing, array technologies, mass spectroscopy, and the like.

In some embodiments, the present invention provides kits for the detection and characterization of cancer (e.g., prostate cancer). In some embodiments, the kits contain antibodies specific for RKIP, or RKIP antibodies in addition to detection reagents and buffers. In other embodiments, the kits contain reagents specific for the detection of RKIP mRNA or cDNA (e.g., oligonucleotide probes or primers). In preferred embodiments, the kits contain all of the components necessary to perform a detection assay, including all controls, directions for performing assays, and any necessary software for analysis and presentation of results.

In preferred embodiments, RKIP is used as a prognostic factor for cancer. Expression of a variety of MSGs have been evaluated for prognosis in multiple cancers. However, there has been no clear documentation that decreased expression of a MSG is prognostic for a cancer. For example, the MSG KAI1 was demonstrated not to be an independent prognostic factor in endometrial cancer (see, e.g., Liu F S, et al., Clin Cancer Res 2003; 9(4):1393-8; herein incorporated by reference in its entirety), cervical cancer (see, e.g., Schindl M, et al., Anticancer Res 2000; 20(6B):4551-5; herein incorporated by reference in its entirety) or ovarian carcinoma (see, e.g., Liu FS, et al., Gynecol Oncol 2000; 78(1):10-5; herein incorporated by reference in its entirety). In fact, increased, as opposed to expected decreased, levels of a KAI1 splice variant was shown to be a poor prognostic factor in gastric cancer (see, e.g., Lee J H, et al., Cancer Res 2003; 63(21):7247-55; herein incorporated by reference in its entirety). Similarly, increased expression of the orphan G-protein-coupled receptor MSG KiSS-1 was shown to indicate a poor prognosis in hepatocellular carcinoma (see, e.g., Ikeguchi M, et al., J Cancer Res Clin Oncol 2003; 129(9):531; herein incorporated by reference in its entirety). Along these lines, increased, as opposed to decreased expression of another MSG, nm23, has been shown to indicate a poor prognosis in multiple cancers including lymphoma (see, e.g., Niitsu N, et al., Leukemia 2003; 17(1):196-202; herein incorporated by reference in its entirety), gastric carcinoma (see, e.g., Muller W, et al., Cancer 1998; 83(12):2481-7; herein incorporated by reference in its entirety), esophageal carcinoma, (see, e.g., Szumilo J, et al., Folia Histochem Cytobiol 2002; 40(4):377-80; herein incorporated by reference in its entirety), breast carcinoma (see, e.g., Galani E, et al., Anticancer Res 2002; 22(4):2275-80; herein incorporated by reference in its entirety) and synovial carcinoma (see, e.g., Golouh R, et al., J Surg Oncol 2001; 76(2):83-8; herein incorporated by reference in its entirety) or have no prognostic value in cancers such as ovarian cancer (see, e.g., Tas F, et al., Am J Clin Oncol 2002; 25(2):164-7; herein incorporated by reference in its entirety) and bladder cancer (see, e.g., Chow N H, et al., Clin Cancer Res 2000; 6(9):3595-9; herein incorporated by reference in its entirety). Another MSG, CD44, was shown not to predict outcome in tongue carcinoma (see, e.g., Masuda M, et al., Head Neck 2000; 22(7):662-5; herein incorporated by reference in its entirety); although in one study it was shown to predict survival (see, e.g., Gonzalez-Moles M A, et al., Anticancer Res 2003; 23(6D):5197-202; herein incorporated by reference in its entirety). Lowered expression of an isoform of CD44 (CD44s) may indicate a poor prognosis in PCa (see, e.g., Noordzij M A, et al., Clin Cancer Res 1997; 3(5):805-15; herein incorporated by reference in its entirety); however, confidence in these results is limited due to very low group numbers (e.g., only 2 or 5 patients in some arms). In a follow-up study, CD44s expression was shown not to be independent prognostic factor in men with PCa (see, e.g., Vis A N, et al., J Pathol 2002; 197(2):148-54; herein incorporated by reference in its entirety). In summary, decreased expression of MSGs has not been clearly demonstrated to be prognostic. Thus, the present invention provides an initial example of a MSG involved in intracellular signaling that is prognostic for cancer recurrence, which demonstrates the importance of evaluating genes that have decreased expression for prognostic value.

Immunohistochemical and gene array data that demonstrate RKIP expression is decreased in metastases provide clinical support for the idea that RKIP is a MSG. The mechanism through which RKIP expression is decreased may involve genetic or epigenetic phenomenon. Regardless of the etiology of decreased RKIP expression, the resulting loss of RKIP activity appears to favor the metastatic process through enhancing invasion and angiogenesis as demonstrated in a murine model (see, e.g., Partin A W, et al., Jama 1997; 277 (18):1445-51; herein incorporated by reference in its entirety). These observations have important implications for the potential mechanism through which PCa gains metastatic ability.

Markers for prognosis of PCa such as preoperative serum PSA level, tumor stage, tumor grade as measured by the Gleason score and surgical margin are limited in their accuracy and prognostic ability (see, e.g., Partin A W, et al., Jama 1997; 277(18):1445-51; herein incorporated by reference in its entirety). For example, preoperative serum PSA level has been identified as a significant independent predictor of clinical outcome in PCa (see, e.g., Zagars G K, et al., Cancer 1993; 72(2):538-48; Bocking A, et al., Anticancer Res 1988; 8(1): 129-35; each herein incorporated by reference in their entireties). However, PSA is not strictly organ-specific, nor is it disease-specific; elevated PSA levels can be found in a small portion of normal men and in many men with BHP and prostatitis. It has been suggested that PSA screening leads to the overdiagnosis and overtreatment of patients with PCa, suggesting that some patients who undergo radical prostatectomy might have lived out their lives without any symptoms of the disease (see, e.g., Etzioni R, et al., J Natl Cancer Inst 2002; 94(13):981-90; herein incorporated by reference in its entirety). In addition, PSA does not correlate well with clinical outcome in patients with PSA values of <10 ng/mL (see, e.g., Stamey T A, et al., J Urol 2002; 167(1):103-11; herein incorporated by reference in its entirety). Similarly, the most commonly used grading system in PCa, Gleason score (see, e.g., Gleason D F, et al., J Urol 1974; 111(1):58-64; Epstein J I, et al., Cancer 1993; 71(11):3582-93; each herein incorporated by reference in their entireties), is most effective as a prognostic factor in tumors with the low (2-4) or high (8-10) scores, but not very effective in the more frequently identified PCa tumors that have an intermediate score (5-7) and show strikingly heterogeneous pathophysiological aggressiveness (see, e.g., Partin A W, et al., Jama 1997; 277(18):1445-51; Schroder F H, et al., J Urol 2000; 163(3):806-12; each herein incorporated by reference in their entireties). Finally, the presence of positive surgical margins indicates an increased risk of progression when compared with negative margins (e.g., Ohori M, et al., J Urol 1995; 154(5):1818-24; herein incorporated by reference in their entireties). However, false-positive margins may result from artifacts induced by difference in surgical techniques, variances in processing radical prostatectomy specimens and in histological evaluation between pathologists (see, e.g., Epstein J I, Urol Clin North Am 1996; 23(4):651-63; herein incorporated by reference in its entirety).

The present invention is not limited to a particular mechanism. Indeed, an understanding of the mechanism is not necessary to practice the present invention. Nonetheless, experiments conducted during the course of the present invention indicate that RKIP is a prognostic factor independent of surgical margin status and minimize difficulties in interpreting surgical margin. The present invention is not limited to a particular mechanism. Indeed, an understanding of the mechanism is not necessary to practice the present invention. Nonetheless, results demonstrate that RKIP is prognostic in patients with PSA<10 ng/ml and with tumors that are Gleason score 6-7 or have positive surgical margins. RKIP offers prognostic benefits above and beyond PSA, Gleason score and surgical margins.

Radical prostatectomy is a definitive form of therapy for clinically localized PCa (see, e.g., Zincke H, et al., J Urol 1994; 152(5 Pt 2):1850-7; herein incorporated by reference in its entirety). After radical prostatectomy, recurrence of the disease in men with negative surgical margin suggests that undetected disease may have spread beyond the prostate gland before surgery (see, e.g., Han M, et al., Urol Clin North Am 2001; 28(3):555-65; Roberts S G, et al., Mayo Clin Proc 2001; 76(6):576-81; each herein incorporated by reference in their entireties). Detecting this population of patients assists toward designing a therapeutic strategy, including aggressive treatment. The present invention is not limited to a particular mechanism. Indeed, an understanding of the mechanism is not necessary to practice the present invention. Nonetheless, the data demonstrates that tumor RKIP expression levels can be used to predict which of these patients will have early PSA recurrence, and thus be used to provide a therapeutic recommendation. Traditional Gleason score did not statistically significantly stratify the risk of this focused set of patients although its clinical implication on prognostication has been demonstrated by many groups (see, e.g., Pettaway Calif., Tech Urol 1998; 4(1):35-42; Blute M L, et al., J Urol 2001; 165(1):119-25; each herein incorporated by reference in its entirety). The present invention is not limited to a particular mechanism. Indeed, an understanding of the mechanism is not necessary to practice the present invention. Nonetheless, the data results indicate that RKIP has overall greater utility than Gleason score in the overall PCa patient population as most patients' tumors fall into the intermediate range of Gleason scores and RKIP is prognostic for this group of patients.

II. Antibodies

The present invention provides isolated antibodies. In preferred embodiments, the present invention provides monoclonal antibodies that specifically bind to an isolated polypeptide comprised of at least five amino acid residues of RKIP. These antibodies find use in the diagnostic methods described herein. In some embodiments, antibodies also find use in research applications, drug screening, and therapeutic applications (e.g., antibodies directed to factors that influence RKIP signaling).

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against RKIP). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against RKIP) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, RKIP protein (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

In some embodiments, antibodies (e.g., monoclonal antibodies) are humanized. Such humanized antibodies find particular use in the cancer immunotherapies described below. Humanized antibodies are altered in order to make them less immunogenic to humans, e.g., by constructing chimeric antibodies in which a mouse antigen-binding variable domain is coupled to a human constant domain. Humanized antibodies are typically human antibodies in which some CDR residues and possibly some FR residues are substituted by residues from analogous sites in rodent antibodies. Methods for humanizing antibodies are well known in the art and include but are not limited to, those disclosed in U.S. Pat. Nos. 6,054,297, 4,816,567, 6,180,377, 5,871,907, 5,585,089, and 6,180,370, each of which is herein incorporated by reference.

III. Drug Screening

In some embodiments, the present invention provides drug screening assays (e.g., to screen for anticancer drugs). In some embodiments, the screening methods of the present invention utilize RKIP. For example, in some embodiments, the present invention provides methods of screening for compounds that alter (e.g., increase) the expression of RKIP. In other embodiments, candidate compounds are antisense agents (e.g., oligonucleotides) directed against inhibitors of RKIP. See Section IV below for a discussion of antisense therapy. In other embodiments, candidate compounds are antibodies (e.g., those described in Section II above and the below Example.

In still further embodiments, candidate compounds are small molecules that mimic the activity of RKIP on downstream signaling proteins, or "RKIP signaling proteins" (e.g., RAF and MEK) and thus restore RKIP function.

A. RKIP Expression Assays

In one screening method, candidate compounds are evaluated for their ability to alter (e.g., increase) RKIP expression by contacting a compound with a cell expressing RKIP and then assaying for the effect of the candidate compounds on expression. In some embodiments, the effect of candidate compounds on expression of RKIP is assayed for by detecting the level of RKIP mRNA expressed by the cell. mRNA expression can be detected by any suitable method, including but not limited to, those disclosed herein.

In other embodiments, the effect of candidate compounds is assayed by measuring the level of RKIP expression. The level of polypeptide expressed can be measured using any suitable method, including but not limited to, those disclosed herein.

In some embodiments, in vitro drug screens are performed using purified wild type RKIP and RAF or MEK. Compounds are screened for their ability to interact with RAF or MEK or other RKIP signaling proteins and inhibit RAF function. In some embodiments, the RAF or MEK proteins are immobilized to facilitate separation of complexed from uncomplexed forms of one or both of the proteins, as well as to accommodate automation of the assay. Binding of a test compound to RAF or MEK or other RKIP signaling proteins is accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-5-transferase/AIP-6 fusion proteins or glutathione-5-transferase/target fusion proteins can be adsorbed onto glutathione sepharose beads (Sigma Chemical; St. Louis, Mo.) or glutathione derivatized microtitre plates, which are then combined with the test compound or the test compound and the non-adsorbed protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of protein binding or activity determined using standard techniques.

Other techniques for immobilizing proteins on matrices can also be used in the screening assays of the invention. For example, downstream RKIP signaling proteins or other protein known to interact with or modulate signaling by RKIP (e.g., RAF or MEK) can be immobilized utilizing conjugation of biotin and streptavidin. Biotinylated proteins are prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with RKIP signaling proteins but which do not interfere with binding of the protein to test compounds can be derivatized to the wells of the plate, and unbound protein trapped in the wells by antibody conjugation. Methods for detecting such complexes, in addition to those described above for the GST-immobilized complexes, include immunodetection of complexes using antibodies reactive with RKIP signaling proteins, as well as enzyme-linked assays that rely on detecting an enzymatic activity associated with RAF.

In other embodiments, a competitive drug screening assays in which neutralizing antibodies capable of binding RKIP signaling proteins specifically compete with a test compound for binding to the RKIP signaling protein are utilized. In this manner, the antibodies can be used to detect the presence of any compound that shares one or more antigenic determinants with RKIP signaling proteins.

In still further embodiments, transgenic animals having altered (e.g., inactivated or overexpressed) RKIP gene are utilized in drug screening applications. For example, in some embodiments, compounds are screened for their ability to reduce metastasis in RKIP null mice.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

IV. Cancer Therapies And Characterization

In some embodiments, the present invention provides therapies for cancer (e.g., prostate cancer) and methods for characterizing (e.g., researching) cancer. In some embodiments, therapies restore RKIP function. In some embodiments, therapies restore RKIP function by providing RKIP protein to a cell (e.g., a cancer cell), tissue, or subject. In other embodiments, therapies restore function by modulating regulators or down stream signaling molecules of RKIP.

A. Genetic And Transplantation Therapies

The present invention contemplates the use of any genetic manipulation for use in modulating the expression of RKIP. Examples of genetic manipulation include, but are not limited to, delivery of RKIP (e.g., to cancer cells, tissues, or subjects). Delivery of nucleic acid construct to cells in vitro or in vivo may be conducted using any suitable method. A suitable method is one that introduces the nucleic acid construct into the cell such that the desired event occurs (e.g., expression of an antisense construct). For example, cells may be transfected ex vivo to increase or induce RKIP expression and the transfected cells may be transplanted to the site of a tumor.

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

B. Antisense and RNAi Therapies

In some embodiments, the present invention targets the expression of RKIP inhibitors or pathway members. For example, in some embodiments, the present invention employs compositions comprising oligomeric antisense compounds, particularly oligonucleotides (e.g., those identified in the drug screening methods described above), for use in modulating the function of nucleic acid molecules encoding RKIP inhibitors, ultimately modulating the amount of RKIP inhibitor expressed or by altering the expression of factors that are overactive or overexpressed in cells or tissues having reduced RKIP. This is accomplished by providing antisense compounds (e.g., antisense oligonucleotides, siRNA, etc.) that specifically hybridize with one or more nucleic acids encoding RKIP inhibitor or pathway component. The specific hybridization of an oligomeric compound with its target nucleic acid interferes with the normal function of the nucleic acid.

C. Antibody Therapy

In some embodiments, the present invention provides antibodies that target RKIP inhibitors or RKIP signal pathway components in tumors (e.g., prostate tumors). In preferred embodiments, the antibodies used for cancer therapy are humanized antibodies.

D. Small Molecule Drugs

In some embodiments, the present invention provides drugs (e.g., small molecule drugs) that prevent metastasis by enhancing or replacing the biological activity of RKIP or altering the biological activity of RKIP regulatory proteins or pathway components. In some embodiments, small molecule drugs are identified using the drug screening methods described above. In particularly preferred embodiments, the small molecule drugs of the present invention result in the cell death of cancer cells or the prevention of metastasis of cancer cells.

In other embodiments, the present invention provides agents that increase RKIP expression. In preferred embodiments, such agents include, but are not limited to, androgen receptor ligands (e.g., dihydrotestosterone).

E. Pharmaceutical Compositions

The present invention further provides pharmaceutical compositions (e.g., comprising the therapeutic compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more therapeutics and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

V. Transgenic Animals Expressing or Lacking RKIP

The present invention contemplates the generation of transgenic animals comprising an exogenous RKIP gene or mutants and variants thereof (e.g., truncations, deletions, insertions, or single nucleotide polymorphisms). In other embodiments, the present invention provides transgenic animals with a knock-out of the RKIP gene. In preferred embodiments, the transgenic animal displays an altered phenotype (e.g., decreased presence of RKIP and increased metastasis) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

Materials and Methods

This example describes methods used in the following examples.

Cell Lines and Cell Cultures

The human prostate cancer cell lines LNCaP (American Type Tissue Collection, Manassas, Va.) and C4-2B cells (Urocor) were grown in T-medium [80% Dulbecco's modified Eagle's medium (GIBCO, Grand Island, N.Y.), 20% F12 (Irving Scientific, Santa Ana, Calif.), 3 g/l $NaCO_3$, 100 units/l penicillin G, 100 µg/ml streptomycin, 5 µg/ml insulin, 13.6 µg/ml triiodothyronine, 5 µg/ml transferrin, 0.25 µg/ml biotin, 25 µg/ml adenine], supplemented with 5% fetal bovine serum (FBS) (See, e.g., Wu, et al., Int J Cancer 77:887-94 (1998); herein incorporated by reference in its entirety). Cells were grown in 150-mm culture dishes in a 37° C. incubator equilibrated with 5% $CO_2$ in humidified air.

Animals 5-6 week-old CB17 SCID (Charles River, Wilmington, Mass.) were housed under pathogen-free conditions in accordance with NIH guidelines using an animal protocol approved by the University of Michigan Animal Care and Use Committee.

Real-Time RT-PCR

Total RNA was extracted using Trizol method as directed by the manufacturer (Life Technologies, Gaithersburg, Md.). 200 ng of total RNA was subjected to real time RT-PCR (LIGHTCYCLER, Roche Diagnostics, Indianapolis, Ind.) using the SYBR Green I RNA amplification kit (Roche Diagnostics, Indianapolis, Ind.). RT-PCR reactions were mixed and then subjected to 45 cycles of 94° C., 5 sec; 55° C., 10 sec; 72° C., 1 min. GAPDH was used as an internal control. The RKIP primers used were purchased from Clontech (Clontech, Palo Alto, Calif.). The RKIP primers used were sense: 5'-CAATGACATCAGCAGTGGCACAGTC-3' (SEQ ID NO: 1) and antisense: 5'-CACATAGTCATCCCACTCGGC-CTG-3' (SEQ ID NO: 2) to generate a 250 bp fragment. The GAPDH primers used were sense: 5'-TGAAGGTCGGTGT-GAACGGATTTGGTC-3' (SEQ ID NO: 3) and antisense, 5'-CATGTAGGCCATGAGGTCCACCAC-3' (SEQ ID NO: 4) to generate a 960 bp fragment.

Subcloning of RKIP cDNA of human RKIP (American Type Tissue Collection, Manassas, Va.) was subcloned into pcDNA3.1(+) and pcDNA3.1(−) expression vectors (Invitrogen, San Diego, Calif.) using BamH I (Life Technologies, Rockville, Md.) and EcoR I (Life Technologies, Rockville, Md.) sites which express sense and antisense-RKIP driven by CMV promoter. To distinguish between pcDNA3.1(+)-ssRKIP and pcDNA3.1 (−)-asRKIP plasmids, the orientation of RKIP cDNA in plasmid clones was analyzed by sequencing and restriction enzyme mapping. Sequence analysis showed 100% homology to the published sequence for RKIP cDNA. As negative controls, the pcDNA3.1(−) and (+) vectors without insert were used in subsequent experiments.

Transfection and Selection

LNCaP cells and C4-2B cells ($5\times10^5$) were transfected with 1 µg of pcDNA3.1 (−)-asRKIP and the pcDNA3.1 (+)-ssRKIP, respectively, using SUPERFECT (QIAGEN, Valencia, Calif.) according to the manufacturer's instructions. Selection was initiated 48 h after transfection by adding 600 µg G418 (Life Technologies, Rockville, Md.)/ml of supplemented culture medium. Selection medium was changed every 4 days for 5 weeks until all nontransfected cells died. Resistant cell clones were isolated and expanded for further characterizations. As negative controls, LNCaP and C4-2B cells were transfected with pcDNA3.1(−) and pcDNA3.1(+), respectively.

In vitro Invasion Assay

The invasiveness of control and sense or antisense-transfected cell clones was evaluated in 24-well transwell chambers (Costar, Cambridge, Mass.) as directed by the manufacturer. Briefly, the upper and lower culture compartments were separated by polycarbonate filters with 8-μm pore size. Some wells were coated with 100 μg/cm² collagen matrix (MATRIGEL, Collaborative Biomedical Products, Bedford, Mass.) that was reconstituted by adding 0.5 ml of serum-free T medium for 2 hours. To establish baseline ability of the cells to cross the membrane, $2.5 \times 10^4$ cells in 0.5 ml of T medium (5% FBS) were placed into the wells without matrix (baseline migration) and 0.75 ml of T medium (10% FBS) was placed in the lower compartment. In parallel, to assess the ability of the cells to invade through matrix, $2.5 \times 10^4$ cells in 0.5 ml of T medium (5% FBS) were placed in wells coated with the reconstituted matrix and 0.75 ml of T medium (10% FBS) was placed in the lower compartment. Assays were incubated for 24 h at 37° C. with 95% air plus 5% $CO_2$. Cell penetration through the membrane was quantified by staining the porous membrane with a Diff-Quik stain kit. The numbers of cells that penetrated through the membrane were counted in five microscopic fields (×200) per filter. Invasive ability was then determined as the proportion of cells that invaded through the matrix-coated membrane relative to the number of cells that migrated through the uncoated membrane (baseline migration). The results are reported as the mean of triplicate assays of the ratio of 100×(the number of cells that penetrate the wells with matrix coat)/(number of cells that penetrate the wells without matrix coat) as presented in FIG. 2.

Immunoblot Analysis

Whole cell lysates were prepared by incubating cells in ice-cold lysis buffer (50 mM Tris-HCl [pH 7.5], 150 mM NaCl, 2 mM EDTA, 50 mM NaF, 1% Triton X-100, 5 μg/ml leupeptin, 5 μg/ml pepstatin, and 0.5 mM phenylmethylsulfonyl fluoride). Cells were sonicated for 8 s and then placed on ice for 15 min. Lysates were precleared, and the protein concentration was determined by the bicinchoninic acid assay (Pierce Biochemicals, Rockford, Ill.). For electrophoresis, lysates were supplemented with SDS loading buffer and separated on SDS-12% polyacrylamide gels. Proteins were transferred to nitrocellulose membranes. The blots were incubated in Tris-buffered saline containing 0.1% Tween 20 and 5% nonfat dry milk during the blocking and the antibody incubation steps. Goat anti-RKIP antibody (SC-5423 and SC-5426; Santa Cruz Biotechnology, Santa Cruz, Calif.) was used at a 1:200 dilution, rabbit anti-actin (Sigma, Saint Louis, Mo.) antibody was used at 1:1,000, and the horseradish peroxidase-conjugated donkey anti-goat (Santa Cruz Biotechnology, Santa Cruz, Calif.) and goat anti-rabbit immunoglobulin (Amersham International, Bucking-Hampshire, England) were used at a 1:5,000 dilution. Antibody complexes were detected by enhanced chemiluminescence (ECL; Amersham Life Science, Arlington Heights, Ill.) and exposure to X-Omat film (Kodak, Rochester, N.Y.). For phosphorylation status of endogenous MEK and ERK in LNCaP, C4-2B cells and their transfectants, cells were lysed and immunoblot analysis for p-MEK or p-ERK by using anti-p-MEK (Cell signaling Technology, Inc, Beverly, Mass.) or anti-p-ERK (Santa Cruz Biotechnology, Santa Cruz, Calif.) was performed. Then, the membranes were stripped and reprobed with anti-MEK or anti-ERK (Santa Cruz Biotechnology, Santa Cruz, Calif.).

Immunohistochemistry (IHC)

Radical prostatectomy specimens were obtained at the time of surgery and frozen in liquid nitrogen within 30 min after surgical excision (see, e.g., Rashid, et al., Cancer Res 61:489-92 (2001); herein incorporated by reference in its entirety). Histological confirmation of both tumor and normal regions of each prostate gland and grading was performed using a protocol that has been previously described (see, e.g., Rubin, et al., JAMA 287:1662-70 (2002); herein incorporated by reference in its entirety). Metastases were obtained and frozen in liquid nitrogen within 4 hours of a patient's death. The metastases were confirmed as prostate cancer in origin by a genitourinary pathologist. Written informed consent was obtained from all patients and all tissue procurement was approved by the University of Michigan Institutional Review Board (IRB).

RKIP protein expression was determined using standard immunoperoxidase IHC. Polyclonal antibody against RKIP (Upstate, Lake Placid, N.Y.) was used as the primary antibody at a concentration of 1:400 dilutions. The bound antibody was visualized by the streptavidin-biotin method including horseradish peroxidase and diaminobenzidine chromogen (HISTOSTAIN KIT, Zymed, San Francisco). Slides were evaluated by a pathologist that was blinded to the samples.

Double-Labeling Immunofluorescence

The tissue sections were incubated overnight at 4° C. in a mixture of goat anti-RKIP (1:50, Santa Cruz Biotechnology, Santa Cruz, Calif.) antibody with rabbit anti-human PSA (1:2000, Dako, Carpenteria, Calif.) antibody. After being washed with PBS, the sections were incubated for two hours at room temperature with a mixture of FITC-labeled anti-rabbit IgG, Texas red-labeled anti-goat IgG (Vector Labs, Burlingame, Calif.) for double staining. Slides were rinsed with PBS and mounted in fluorescence mounting medium (Vector lab, Burlingame, Calif.). Images were obtained using a Carl Zeiss fluorescence microscope (Carl Zeiss, New York, N.Y.). Specificity studies, performed by omitting then primary antibody, demonstrated the absence of the fluorescent signal. As an additional control, it was tested whether the secondary antibody used in the double labeling were specific and did or did not cross react. To test for this possibility, one of the primary antibodies was incubated alone and revealed by both secondary antibodies. The nonspecific staining was totally abolished without alteration of the specific staining.

Growth Curve

Cell proliferation was measured using the CellTiter 96 AQ Non-radioactive cell proliferation assay (Promega, Madison, Wis.). Briefly, cells were plated in 96-well plates at a density of 500 cells/well in T medium. Cells were allowed to grow for 2, 4, 6, and 8 days, then 20 μl/well of combined MTS/PMS solution was added. After incubation for two hour at 37° C. in a humidified 5% $CO_2$ atmosphere, the absorbance was measure at 490 nm by using an ELISA plate reader. Data presented represent the average of six wells in one experiment which was repeated twice with similar results.

Colony Formation in Soft Agar

Assays of colony formation in soft agar were performed using routine methods. Briefly, 1 ml underlayers of 0.6% agar medium were prepared in 35-mm dishes by combining equal volumes of 1.2% Noble agar and 2×T medium with 10% FBS (Difco, Detroit, Mich.). The cells were trypsinized, centrifuged, and resuspended, and $10^4$ cells were plated in 0.3% agar medium. The surface was kept wet by addition of a small amount of growth medium. After 5 to 6 weeks, dishes were stained with methylene blue and colonies were photographed and counted.

Spontaneous Metastasis Assays

To characterize the in vivo growth rate and metastatic ability of the transfected clones, 5-6-week-old CB 17 severe combination immunodeficient mice (SCID) (Charles River Laboratories, Wilmington, Mass.) were injected orthotopically with pools of C4-2B cells stably transfected with either control vector or RKIP cDNA (1×10$^6$ cells) into dorsolateral lobe of the prostate gland by a 30-gauge needle (BD, San Diego, Calif.). In order to minimize clonal specificity, pooled clones were used. Specifically, for C4-2B stably transfected with control vector, C4-2B-(+)#3 and C4-2B-(+)#4 were pooled together; whereas, for C4-2B stably transfected with sense RKIP, C4-2B-ssRKIP#2, C4-2B-ssRKIP#5, and C4-2B-ssRKIP#9 were pooled together (each clone was represented in equal parts).

Tumor volume was determined using the formula for hemiellipsoids: V=length×width×height×0.5236. 70 days after injection, animals were sacrificed, the lungs were excised, fixed in 10% formalin, embedded, sectioned, and stained with hematoxylin and eosin. Additionally, to help identify lung metastases, sections were stained for PSA and quantified (see, e.g., Wang, et al., Prostate 39:182-6 (1999); herein incorporated by reference in its entirety).

Statistical Analysis

The trend of RKIP expression levels over benign and increasing Gleason score of cancerous tissue through metastatic tissue was tested using the Mantel-Haenszel Chi-square test. For in vivo spontaneous metastasis assays, the difference in tumor size, number of lung metastases per mouse (of those which developed metastases), and percentage of vessels that were invaded (of those with any invasion) between RKIP transfectants and control transfectants were tested using the non-parametric Wilcoxon rank-sum Test. Rates of lung metastases development and vessel invasion were compared between the two groups using Fisher's Exact Test. For in vitro studies, single comparisons were performed using Student's t test and multiple comparisons were performed using one-way analysis of variance (ANOVA) with Fisher's protected least significant difference for post-hoc analysis. Statistical tests were two-sided. For all tests, the level of significance was set at $P<0.05$. Statistical calculations were performed using SAS System (Cary, N.C.).

Example 2

RKIP Expression in Metastatic Prostate Cancer

To confirm previous gene array findings that RKIP expression is decreased in the C4-2B metastatic prostate cancer cell line compared to its non-metastatic parental LNCaP cell line (see, e.g., Fu, et al., Prostate 51:10-20 (2002); herein incorporated by reference in its entirety) RKIP mRNA and protein levels were measured in these cell lines. Real-time RT-PCR demonstrated that RKIP mRNA level was 4 to 5-fold lower in C4-2B than that in LNCaP (FIG. 1), while immunoblot showed that the protein level was about 3-fold lower in the C4-2B cells compared to LNCaP cells (FIG. 1).

To determine if these findings had relevance to clinical prostate cancer, RKIP protein expression was evaluated in prostate cancer tissue. RKIP was present in all non-cancerous (n=10) and primary cancers (n=12) examined, but it was undetectable in all metastases examined (n=22) (see Table 1 below). Specifically, RKIP expression level was highest for benign tissue, lower for cancerous tissue (declining with increasing Gleason score), and absent in metastases ($p<0.0001$, Mantel-Haneszel Chi-square test).

TABLE 1

Expression of raf kinase inhibitor protein (RKIP) in prostate cancer tissues*.

| Tissue | Gleason score | Number evaluated | RKIP expression (95% confidence interval) |
|---|---|---|---|
| Non cancerous | | 10 | 3.0(3.0-3.0) |
| Primary CaP | 6 | 2 | 2.0(2.0-2.0) |
| Primary CaP | 7 | 6 | 1.6(1.1-2.1) |
| Primary CaP | 8 | 4 | 0.5(−0.1-1.1) |
| CaP metastases† | | 22 | 0.0(0.0-0.0) |

*The staining intensity was scored as following: 0 (negative), 1 (weak), 2 (moderate), or 3 (strong).
†The metastases examined were from lymph nodes (3 cases), bone (3 cases), liver (7 cases), lung (2 cases), adrenal (2 cases), and miscellaneous (5 cases).

Example 3

RKIP Expression Level and Cellular Invasiveness in Prostate Cancer Cells

Figure 2:
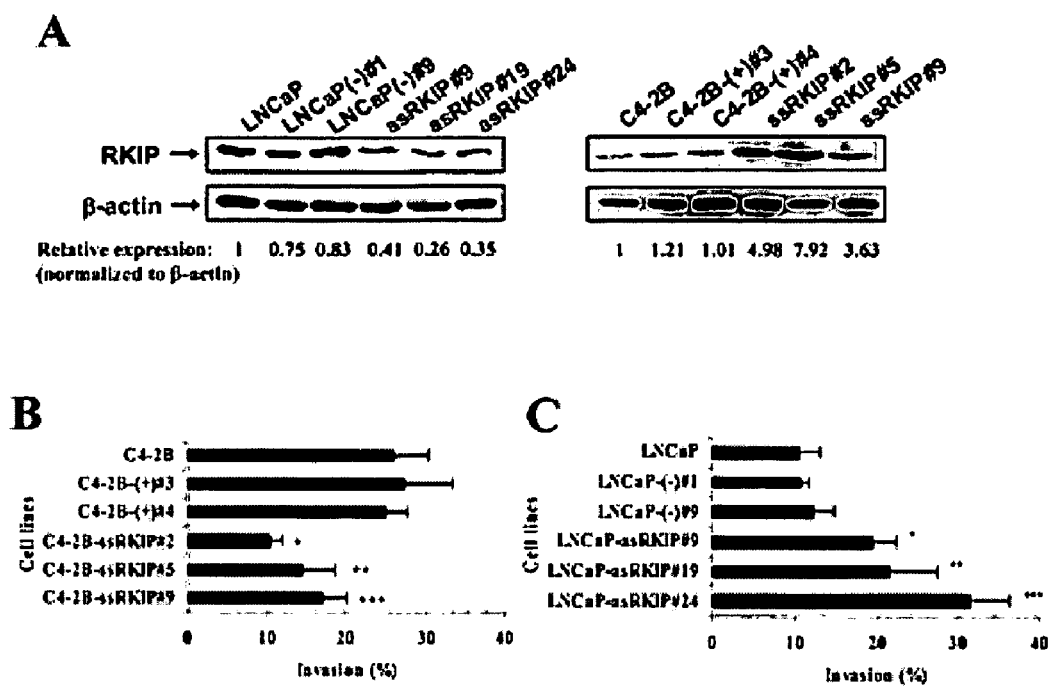
FIG. 2 presents an in vitro invasion assay of LNCaP and C4-2B transfected with antisense and sense raf kinase inhibitor protein (RKIP), respectively. A) Representative immunoblot demonstrating expression of RKIP in C4-2B and LNCaP and their transfectants (40 µg total cellular protein loaded in each lane). B) The in vitro invasiveness of wildtype C4-2B cells and several control (+) and RKIP sense (ss) stably-transfected clones. C) The in vitro invasiveness of wildtype LNCaP cells and several control (−) and antisense (as) stably-transfected clones.

To characterize the function of RKIP during prostate cancer progression, RKIP expression was modulated in prostate cancer cells. RKIP cDNA (or empty expression vector for control) was stably transfected into C4-2B cells to increase RKIP expression and stably transfected LNCaP cells with antisense RKIP cDNA (or empty expression vector for control) to decrease RKIP expression. The sense-transfected C4-2B cells demonstrated increased RKIP expression and the antisense-transfected LNCaP cells demonstrated decreased RKIP expression compared to the control-transfected cells (FIG. 2).

To determine if modulation of RKIP expression influences tumorigenic properties, measurements were obtained of in vitro proliferation rates and colony formation ability in soft agar of the various LNCaP and C4-2B transfected clones. There was no difference of in vitro proliferation rates or colony formation between the control-transfected and sense-transfected (C4-2B) or antisense-transfected (LNCaP) clones. The present invention is not limited to a particular mechanism, and an understanding of a mechanism is not necessary to practice the present invention. Nonetheless, these data suggest that modulation of RKIP expression has no effect on primary tumorigenic properties.

Invasion is one of the key components of the metastatic cascade. Accordingly, to determine if RKIP expression is associated with invasiveness, in vitro invasive ability of parental LNCaP and C4-2B cells and their transfectants was evaluated. Increasing the expression of RKIP with sense RKIP cDNA decreased in vitro invasive ability of C4-2B cells between 30-50% (FIG. 2). In agreement with this observation, decreasing RKIP expression in LNCaP cells with antisense RKIP cDNA increased their in vitro invasive ability by 30-100% (FIG. 2). The present invention is not limited to a particular mechanism, and an understanding of a mechanism is not necessary to practice the present invention. Nonetheless, these results show that RKIP is negatively correlated with invasiveness of prostate cancer cells in vitro.

Example 4

RKIP in an In Vivo Model of Metastasis Suppression

To determine if restoration of RKIP expression reverses the metastatic phenotype of C4-2B cells, pooled clones of C4-2B cells stably transfected with either control vector or RKIP cDNA were implanted into the dorsal lobe of the prostate in mice. Two independent experiments and their pooled results are reported in Table 2. Ten weeks after the orthotopic implantation of tumor cells, there was no difference in size of the primary tumors between the RKIP-transfected and control vector-transfected cells. However, restoring RKIP expression in the C4-2B cells resulted in a decreased number of animals with metastases compared to those animals receiving the control-transfected cells (see Table 2 below). Furthermore, of the three animals that received the C4-2B with RKIP cDNA and developed metastases, the average number of lung metastases was decreased by 89% compared to the animals that received the control-transfected cells (see Table 2).

evaluated. Vascular invasion was identified in 10/10 mice with the C4-2B vector-transfected tumors compared to only 4/10 mice with the C4-2B RKIP-transfected tumors (P=0.01, Fisher's Exact Test). Additionally, the proportion of blood vessels invaded by tumor cells in the primary orthotopic tumors was determined. It was observed that in the mice with C4-2B control-transfected tumors (n=10 mice) that on average 22.0% of the vessels in the primary tumors were invaded and that all 10 mice had vascular invasion of at least 10.5%. In contrast, of the 4 mice with the C4-2B sense RKIP-transfected tumors that demonstrated vessel invasion, on average 3.0% of the vessels had tumor invasion, and all 4 mice had

TABLE 2

Reduced metastatic ability of C4-2B after transfection with human raf kinase inhibitor protein (RKIP) cDNA*.

| Cell lines | Primary tumor formation | Tumor size (cm³) | No. of mice with lung metastases | No. of lung metastases/mouse |
|---|---|---|---|---|
| Experiment 1 | | | | |
| C4-2B-(+) | 5/5 | 2.25, 1.69, 1.87, 1.61, 1.43 | 5/5 | 15, 79, 17, 12, 18 |
| C4-2B-ssRKIP | 5/5 | 2.14, 2.06, 2.36, 2.35, 1.59 | 2/5 | 0, 4, 0, 3, 0 |
| Experiment 2 | | | | |
| C4-2B-(+) | 5/5 | 1.71, 2.81, 2.17, 2.63, 1.80 | 5/5 | 12, 54, 18, 17, 21 |
| C4-2B-ssRKIP | 5/5 | 2.59, 2.20, 1.44, 2.49, 1.70 | 1/5 | 0, 5, 0, 0, 0 |
| Total | | | | |
| C4-2B-(+) | 10/10 | | 10/10 | |
| C4-2B-ssRKIP | 10/10 | 2.20 (1.89-2.51)† 2.09 (1.81-2.37)§ | 3/10‖ | 26.30 (10.45-42.15)‡ 4.00 (1.52-6.48)¶ |

*Spontaneous metastatic ability was determined by injection of 1 × 10⁶ cells C4-2B vector-transfected cells or RKIP sense-transfected cells orthotopically into ten animals and quantification of the number of lung metastases 70 days after injection (Lung sections were stained for prostate specific antigen (PSA) expression to identify lung metastases).
†Mean of the tumor sizes (95% confidence interval).
‡Mean of number of lung metastases per mice with lung metastasis developed (95% confidence interval).
§P = 0.4727 compared to C4-2B control-transfected cells (Wilcoxon rank sum test).
‖P = 0.0031 compared to C4-2B control-transfected cells (Fisher's exact test).
¶P = 0.0139 compared to C4-2B control-transfected cells (Wilcoxon rank sum test).

To confirm that RKIP expression was modulated in vivo, RKIP protein expression using immunohistochemistry in primary tumors and metastases was evaluated. RKIP expression was increased in the RKIP-transfected C4-2B primary tumors compared to the control-transfected C4-2B primary tumors. RKIP was not detectable in the metastases from the control-transfected C4-2B cell primary tumors. Furthermore, although RKIP expression was readily detectable in the RKIP-transfected C4-2B cell primary tumors expressed, RKIP was not detectable in the few metastases that developed from them. The present invention is not limited to a particular mechanism, and an understanding of a mechanism is not necessary to practice the present invention. Nonetheless, this latter observation demonstrates that RKIP expression was down-regulated in the metastases.

Example 5

RKIP and Prostate Cancer Invasion

To determine if invasion contributes to the mechanism through which decreased RKIP expression promotes metastasis, the degree of vascular invasion in the primary orthotopic tumors from the mice injected with control-transfected or sense RKIP cDNA-transfected C4-2B cells was vascular invasion of less than 4.9%. The present invention is not limited to a particular mechanism, and an understanding of a mechanism is not necessary to practice the present invention. Nonetheless, these results demonstrate that RKIP significantly repressed vascular invasion by the C4-2B cells (P=0.01, Wilcoxon rank-sum Test).

Example 6

RKIP Expression and Angiogenesis in Tumors

Angiogenesis is a critical factor in the establishment of primary and metastatic tumors. Accordingly, the total number of vessels per a primary tumor core section in the mice was evaluated. It was found that the tumors that developed from the control-transfected C4-2B cells had 118.1 vessels (95% confidence interval=97.2 to 139.0) per tumor compared to 50.1 vessels per tumor (95% confident interval=25.2 to 75.0) in the tumors from the RKIP-transfected C4-2B cells. To determine if differences in vascular endothelial growth factor (VEGF) expression could account for the differing vascularity of the tumors, VEGF production by the two cell lines was measured.

Example 7

Figure 3:
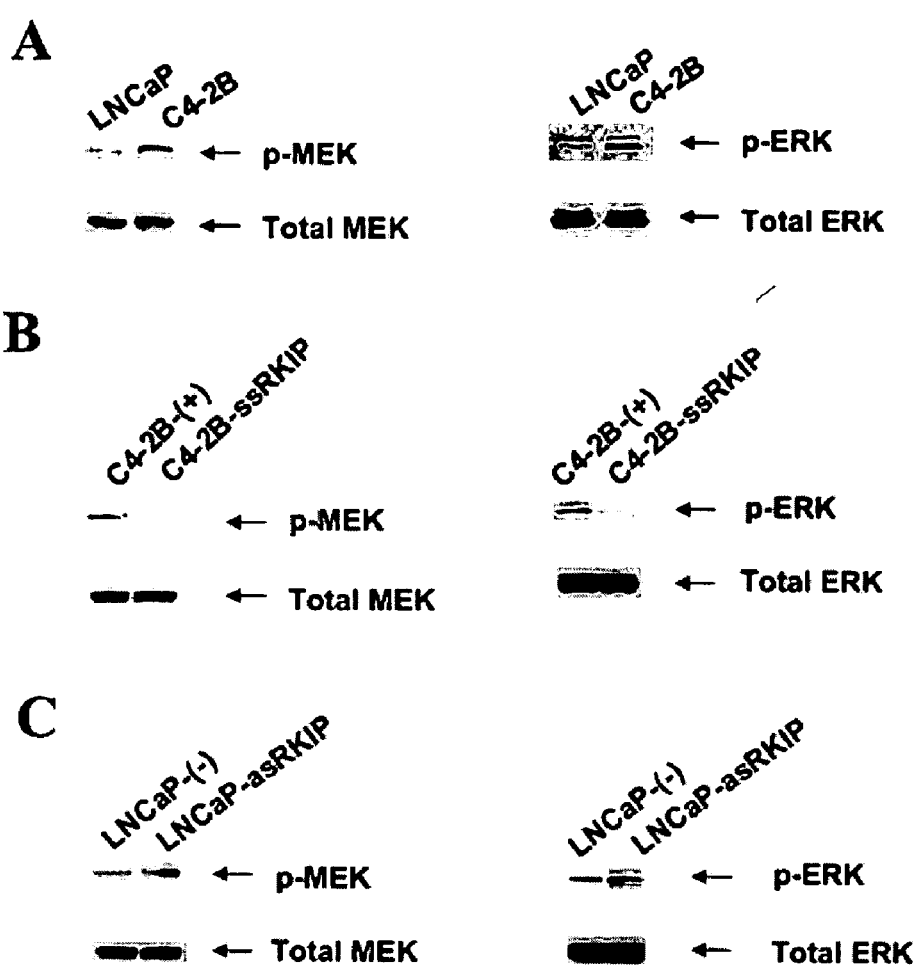
FIG. 3 shows modulation of raf kinase inhibitor protein (RKIP) expression alters MEK and ERK activation in prostate cancer cells. A) Immunblot analysis for phosphorylated (p)-MEK or p-ERK in non-transfected LNCaP and C4-2B cells. B) Immunoblot analysis for p-MEK and p-ERK in vector-transfected or RKIP sense (ss)-transfected C4-2B cells. C) Immunoblot analysis for p-MEK and p-ERK in vector-transfected or RKIP antisense (as)-transfected LNCaP cells.

RKIP's Modulation of Raf/MEK/ERK Signaling in the Invasive Ability of Prostate Cancer Cells To determine if the diminished RKIP expression identified in prostate cancer metastases could affect endogenous signaling molecules downstream of Raf, the phosphorylation status of MEK and ERK in sense and antisense RKIP transfectants. The total MEK and ERK expression were the same in the LNCaP and C4-2B cells; however, basal levels of phosphorylated MEK and ERK were higher in the C4-2B cells (FIG. 3). Increasing RKIP expression in C4-2B cells reduced phosphorylated MEK and ERK expression (FIG. 3); whereas, decreasing RKIP expression increased phosphorylated MEK and ERK expression in LNCaP cells (FIG. 3). Again, the level of RKIP expression had no influence on total MEK or ERK expression (FIG. 3). The present invention is not limited to a particular mechanism, and an understanding of a mechanism is not necessary to practice the present invention. Nonetheless, these data demonstrate that spontaneous decrease of RKIP expression (LNCaP vs. C4-2B cells) promotes MEK and ERK phosphorylation. Furthermore, they demonstrate that modulation of RKIP expression is associated with concurrent changes in phosphorylation status of MEK and ERK in prostate cancer cells.

Figure 4:
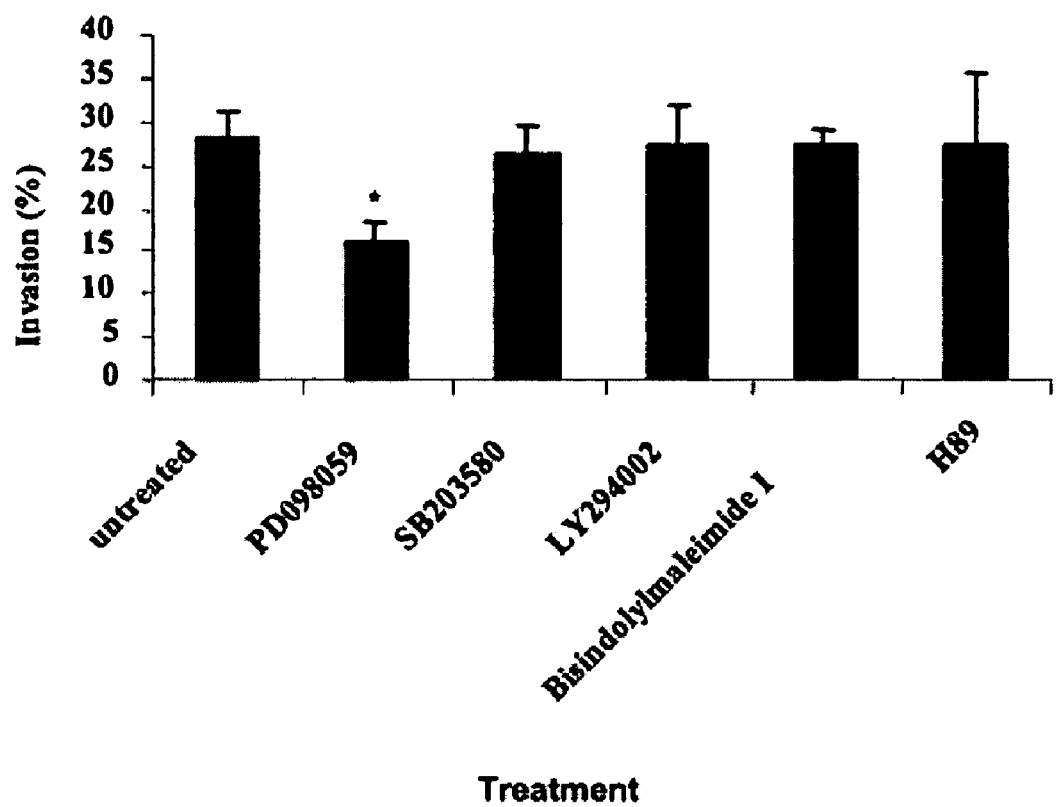
FIG. 4 shows the invasiveness of C4-2B cells in the presence and absence of the indicated protein kinase inhibitors. Bars represent the mean and the upper 95% confidence interval.

Furthermore, because RKIP inhibits tumor invasiveness, it was investigated whether RKIP exerts its metastasis suppressor gene function through regulation of MEK activation. It was tested whether Raf/MEK/ERK signaling induces prostate cancer invasion. Accordingly, the effect of a variety of kinase inhibitors was evaluated, including a MEK inhibitor (PD098059) on in vitro invasion. PD098059 decreased the invasive ability of C4-2B cells by 41%; whereas the other kinase inhibitors had no effect (FIG. 4). The present invention is not limited to a particular mechanism, and an understanding of a mechanism is not necessary to practice the present invention. Nonetheless, these data show that RKIP regulates tumor invasion through inhibition of MEK activity.

Example 8

Associations of RKIP IHC Staining with Tissue Type and Clinical Factors

Figure 5:
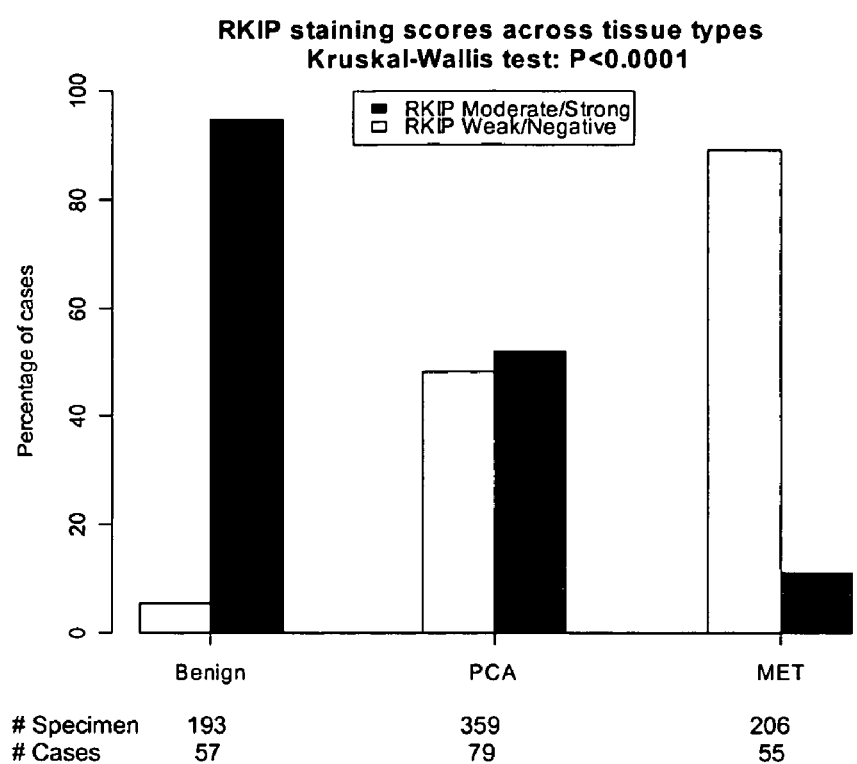
FIG. 5 shows RKIP staining intensity across tissue types.

This example describes the association of RKIP staining with prostate cancer. These data demonstrate that loss of RKIP is associated with increasing Gleason score (i.e., more aggressive tumor) and higher stage of tumor (i.e., more advanced tumor). Thus, these data demonstrate the utility of measuring RKIP expression as an indicator of how advanced the prostate cancer is. FIG. 5 shows RKIP staining intensity across tissue types. Median intensity scores of RKIP was used for each case and the median scores were then dichotomized into RKIP moderate/strong (median score>=3) and RKIP weak/negative (median score<3). Percentages of the dichotomized staining scores were represented by the corresponding bars for each of the three tissue types. Metastatic cases are from TMA45a and TMA54 (warm autopsy specimen) combined. Localized cases are from TMA7a and TMA35 combined. Benign cases include normal, benign and PIN. Kruskal-Wallis test of linear trend of association between RKIP staining and tissue type gives a p-value less than 0.0001. Mean staining intensity on a scale of 1-4 is 3.42 (±0.62) for Benign, 2.57 (±0.73) for PCA, and 2.03 (±0.56) for Mets. Table 3 shows RKIP staining associated with clinical parameters (84 PCA cases).

TABLE 3

| Clinical parameter | | RKIP Weak/negative | RKIP Moderate/strong | test | P |
|---|---|---|---|---|---|
| | | Number of cases (%) | | | |
| Gleason | <=6 | 10 (32.3) | 21 (67.7) | Wilcoxon | 0.02 |
| | >6 | 28 (58.3) | 20 (41.7) | | |
| Tumor size | <=2 cm | 30 (50.8) | 29 (49.2) | Wilcoxon | 0.40 |
| | >2 cm | 8 (40.0) | 12 (60.0) | | |
| Lymph node | | Majority lymph node negative (3 positive) | | | |
| ClinStage | T2 | 25 (41.7) | 35 (58.3) | Wilcoxon | 0.04 |
| | T3 | 13 (68.4) | 6 (31.6) | | |
| SM | Negative | 31 (58.5) | 22 (41.5) | Wilcoxon | 0.09 |
| | Positive | 10 (38.5) | 16 (61.5) | | |
| DRE | Negative | 22 (44.9) | 27 (55.1) | Wilcoxon | 0.47 |
| | Positive | 16 (53.3) | 14 (46.7) | | |
| PSA | Ln(PSA) | Ln(psa) as a continuous covariate | | Cochran-Armitage | 0.59 |
| Gland Weight | | GW as a continuous covariate | | Cochran-Armitage | 0.28 |

Table 3 is based on the 79 localized prostate cancer cases from TMA07 and TMA35 combined. RKIP was treated as a dichotomous variable defined previously. Different types of tests were applied to test for a linear trend of association between RKIP and each of the factors listed in the table. Wilcoxon tests were applied when the covariate divides into two groups. Kruskal-Wallis tests were applied when the covariate has more than two groups, and Cochran-Armitage tests were applied when the factor is on continuous scale.

Example 9

RKIP Predicts PSA Recurrence

Figure 6:
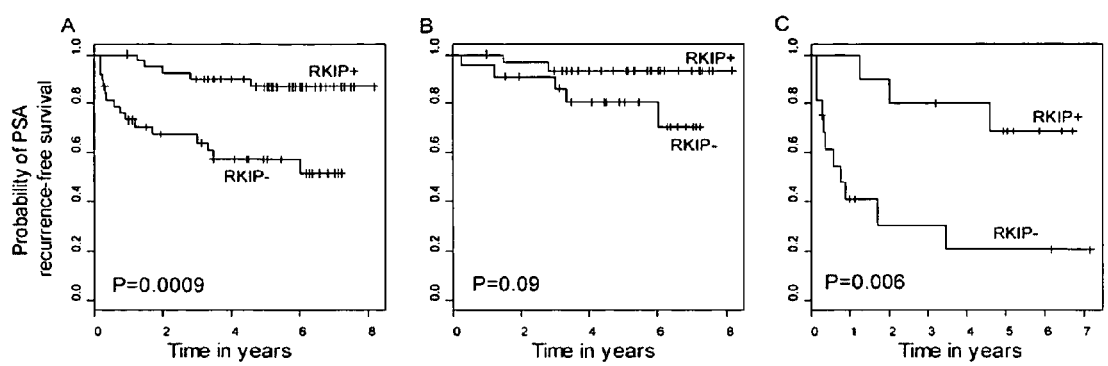
FIG. 6 shows Kaplan-Meier curves of estimated probability of PSA recurrence-free survival.

This example describes the association of RKIP expression with prostate cancer recurrence. These data demonstrate that RKIP expression in the primary tumor is a strong predictor of PSA recurrence. Specifically, low RKIP expression is associated with shorter time to PSA recurrence. FIG. 6 and Table 4 show Kaplan-Meier curves of estimated probability of PSA recurrence-free survival.

TABLE 4

| | All (n = 79) | | SM Negative (n = 53) | | SM Positive (n = 26) | |
|---|---|---|---|---|---|---|
| | Recurred | Censored | Recurred | Censored | Recurred | Censored |
| RKIP+ | 5 | 36 | 5 | 17 | 11 | 5 |
| RKIP− | 16 | 22 | 2 | 29 | 3 | 7 |
| | Kaplan-Meier survival estimates | | | | | |
| | Two-year | Five-year | Two-year | Five-year | Two-year | Five-year |
| RKIP+ | 0.92 | 0.87 | 0.97 | 0.97 | 0.80 | 0.69 |
| | (0.85, 1.00) | (0.76, 0.98) | (0.90, 1.00) | (0.90, 1.00) | (0.59, 1.00) | (0.44, 1.00) |
| RKIP− | 0.67 | 0.57 | 0.91 | 0.81 | 0.31 | 0.20 |
| | (0.53, 0.84) | (0.43, 0.77) | (0.80, 1.00) | (0.65, 1.00) | (0.13, 0.70) | (0.06, 0.65) |

Strata: RKIP

Tables 5, 6 and 7 show Cox regression analysis of PSA recurrence on RKIP and different clinical factors assuming proportional hazards over time. SM refers to surgical margin; RKIP refers to RKIP expression, PSA refers to PSA score, and DRE refers to Digital rectal exam.

TABLE 5

Univariate Cox regression models

| Factor | N | Wald p-value | Hazard Ratio | 95% confidence interval for HR | |
|---|---|---|---|---|---|
| RKIP | 79 | 0.002 | 0.21 | 0.08 | 0.58 |
| Gleason | 79 | 0.23 | 1.80 | 0.70 | 4.63 |
| Tumor size | 79 | 0.009 | 3.15 | 1.34 | 7.42 |
| Path stage | 79 | 0.003 | 3.70 | 1.57 | 8.74 |
| SM | 79 | <0.0001 | 6.34 | 2.54 | 15.80 |
| DRE | 79 | 0.25 | 1.66 | 0.71 | 3.91 |
| PSA | 79 | 0.002 | 2.46 | 1.39 | 4.36 |
| Gland Weight | 79 | 0.45 | 0.99 | 0.96 | 1.02 |

TABLE 6

Multivariate Cox regression models

| Factor | N | Wald p-value | Hazard Ratio | 95% confidence interval for HR | |
|---|---|---|---|---|---|
| RKIP | 79 | 0.0005 | 0.11 | 0.03 | 0.38 |
| Gleason | 79 | 0.10 | 0.38 | 0.12 | 1.20 |
| Tumor size | 79 | 0.63 | 1.29 | 0.46 | 3.60 |
| Path stage | 79 | 0.66 | 1.33 | 0.36 | 4.88 |
| SM | 79 | 0.0008 | 6.72 | 2.21 | 20.49 |
| DRE | 79 | 0.53 | 1.48 | 0.43 | 5.07 |
| Ln(PSA) | 79 | 0.007 | 2.91 | 1.33 | 6.37 |
| Gland Weight | 79 | 0.93 | 1.00 | 0.96 | 1.03 |

TABLE 7

Multivariate Cox regression models (RKIP + SM + ln(PSA))

| Factor | N | Wald p-value | Hazard Ratio | 95% confidence interval for HR | |
|---|---|---|---|---|---|
| RKIP | 79 | 0.0005 | 0.15 | 0.05 | 0.44 |
| SM | 79 | <0.0001 | 6.73 | 2.62 | 17.32 |
| Ln(PSA) | 79 | 0.0003 | 3.15 | 1.68 | 5.88 |

Surgical margin (SM) (P=0.003) and ln(PSA) (P=0.01) were found to be the two independent clinical factors in a multivariate model with all clinical parameters. See Table 8.

TABLE 8

Multivariate Cox model with clinical parameters

| Factor | n | Wald p-value | Hazard Ratio | 95% confidence interval for HR | |
|---|---|---|---|---|---|
| Gleason | 79 | 0.75 | 0.84 | 0.29 | 2.42 |
| Tumor size | 79 | 0.60 | 1.82 | 0.65 | 5.13 |
| Path stage | 79 | 0.65 | 1.32 | 0.40 | 4.43 |
| SM | 79 | 0.003 | 5.05 | 1.76 | 14.51 |
| DRE | 79 | 0.40 | 1.57 | 0.55 | 4.46 |
| Ln(PSA) | 79 | 0.01 | 2.76 | 1.23 | 6.21 |
| Gland Weight | 79 | 0.64 | 0.99 | 0.96 | 1.02 |

Example 10

IL-6 Reduces RKIP Expression in LNCaP Prostate Cancer Cells

Figure 7:
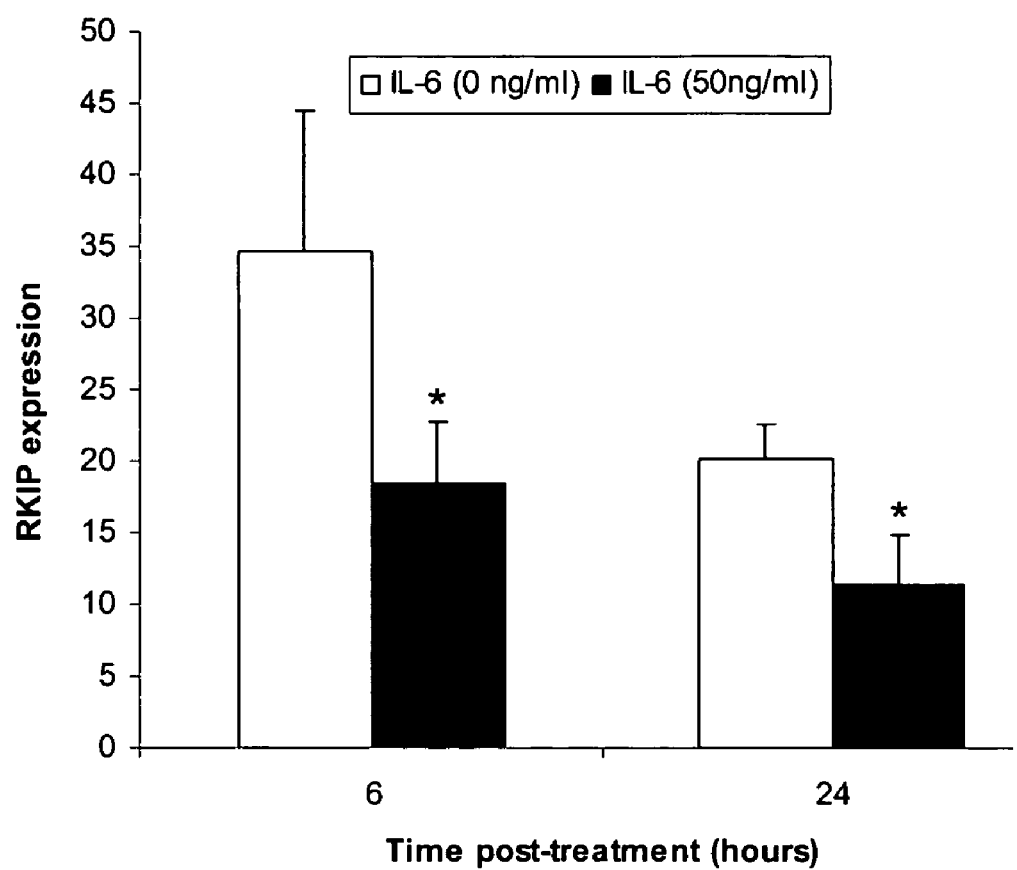
FIG. 7 shows that IL-6 reduces RKIP expression in LNCaP prostate cancer cells.

This example demonstrates that IL-6 reduces RKIP expression in LNCaP prostate cancer cells. LNCaP cells were plated in culture dishes and treated with IL-6 (50 ng/ml) or vehicle for 6 or 24 hours. Total RNA was collected and subjected to real time PCR for RKIP mRNA levels. RKIP mRNA levels were normalized to β-galactosidase mRNA levels. The results are shown in FIG. 7.

The cytokine interleukin-6 (IL-6) is elevated in the serum of men with progressive prostate cancer and IL-6 has been shown to promote tumor progression. (Smith et al, (2001) Cytokine Growth Factor Rev 12, 33-40). The present invention is not limited to a particular mechanism. Indeed, an understanding of the mechanism is not necessary to practice the present invention. Nonetheless, it is contemplated that, since IL-6 downregulates RKIP expression (FIG. 7), that loss of RKIP may be a mechanism through which IL-6 promotes prostate cancer progression. These results suggest that targeting the RKIP pathway may help prevent IL-6-mediated tumor progression.

Example 11

Microarray Analysis from Meta-Analysis of Oncomine Database

This Example describes the expression RKIP transcript in cancer tissues was obtained from meta-analysis of a recently established cancer gene microarray meta-analysis public database (see, e.g., Rhodes D R, Yu J, Shanker K, et al.

Neoplasia 2004; 6(1): 1-6; herein incorporated by reference in its entirety). The normalized expression unit for RKIP transcript was exported and subjected to statistical analysis.

Figure 8:
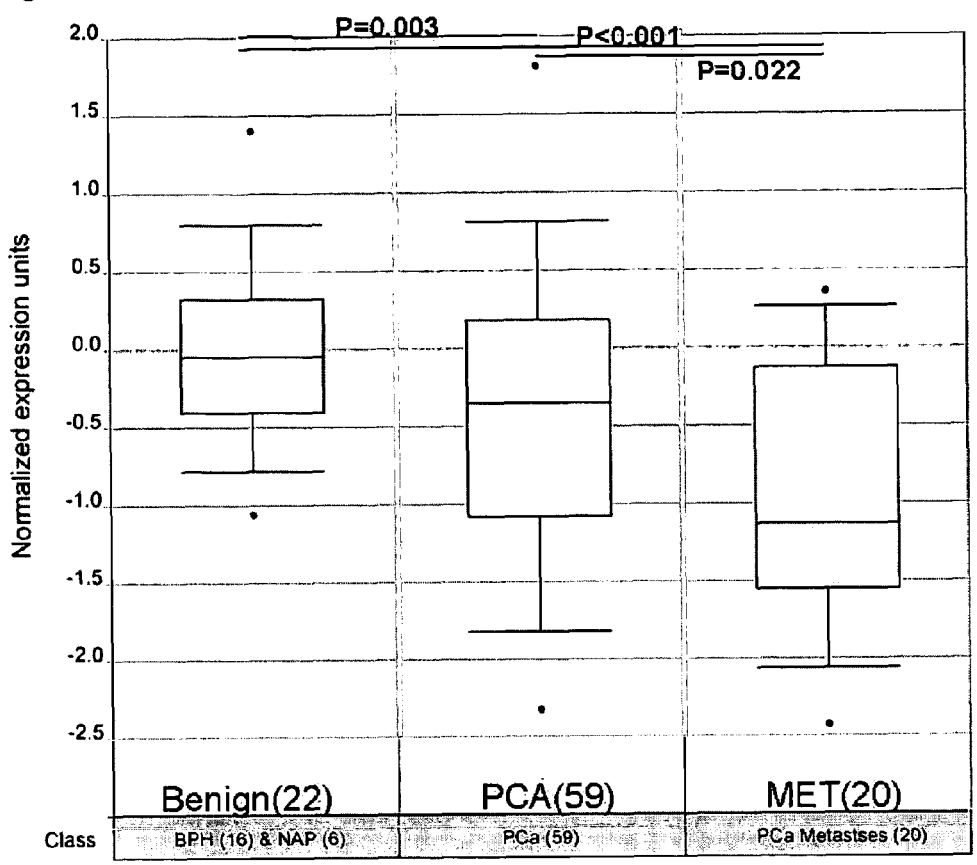
FIG. 8 shows RKIP mRNA transcript levels are decreased in prostate cancer (PCa). RKIP mRNA transcript levels in PCa progression as measured using Oncomine analysis of DNA microarrays. 22 cases of benign prostate, 59 cases of localized PCa, 20 cases of metastatic PCa were included in the study. Y axis represents normalized expression units. P value was calculated by using the Student's t test.

Analysis of gene expression data sets from a recently established cancer gene microarray meta-analysis public database (see, e.g., Rhodes D R, et al., Neoplasia 2004; 6(1): 1-6; herein incorporated by reference in its entirety) demonstrated decreased RKIP expression with advanced cancer (FIG. 8). Specifically, Dhanasekaran et al. investigated gene expression patterns in non-cancerous prostate, localized PCa and metastatic PCa (see, e.g., Dhanasekaran S M, et al., Nature 2001; 412(6849):822-6; herein incorporated by reference in its entirety). Analysis of this dataset revealed that RKIP mRNA expression was significantly lower in localized PCa than that in non-cancerous prostate samples (P=0.003, Student's t test). Furthermore, metastatic PCa has statistically significantly lower RKIP mRNA expression relative to both non-cancerous prostate tissues (P<0.001, Student's t test) and localized PCa (P=0.021, Student's t test) (FIG. 8). These data are in agreement with previous findings in PCa cell lines (see, e.g., Fu Z, et al., J Natl Cancer Inst 2003; 95(12):878-89; herein incorporated by reference in its entirety). As these results show, RKIP mRNA expression declines with PCa progression.

Example 12

Tissue Microarray Analysis

This Example describes tissue microarray analysis to study the expression of RKIP in PCa. Cases of clinically localized PCa were identified from a radical prostatectomy series and cases with PCa metastases were obtained from a Rapid Autopsy Program. The autopsy protocol and initial characterization of these cases have been reported (see, e.g., Rubin M A, et al., Clin Cancer Res 2000; 6(3):1038-45; herein incorporated by reference in its entirety). Briefly, all the patients had well-documented metastatic PCa. Autopsies were performed within 4-6 h of the patient's death. Autopsy revealed widespread PCa involving multiple sites. No other primary malignancy was found. Standard demographic and treatment history parameters were recorded.

To study the expression of RKIP in PCa, tissue microarrays (TMAs) that consisted of a total of 758 evaluable samples of non-neoplastic prostate (n=57), localized PCa (n=79) and metastatic, hormone-refractory PCa (n=55) were used. All 79 patients with localized PCa underwent prostatectomy to treat their localized disease. The metastatic TMAs included PCa metastatic to the liver, lung, bone, lymph node, brain, adrenal, and soft tissue. At least six 0.6-mm cores were taken from each sample. High-density TMAs were assembled as previously described (see, e.g., Perrone E E, et al., J Natl Cancer Inst 2000; 92(11):937-9; Kononen J, et al., Nat Med 1998; 4(7):844-7; each herein incorporated by reference in their entireties). Initial sections were stained for haematoxylin and eosin to verify histology. The histological grade was assessed using the Gleason grading system according to previously described methods (see, e.g., Gleason D F, Cancer Chemother Rep 1966; 50(3): 125-8; herein incorporated by reference in its entirety). Clinical and pathological variables were determined following well-established criteria and maintained in a secure relational database as previously described (see, e.g., Manley S, et al., Am J Pathol 2001; 159(3):837-43; herein incorporated by reference in its entirety).

For analysis of gene microarray data, Student's t test was used for pair-wise comparison of RKIP transcript among benign prostate, localized PCa and metastatic PCa samples as previously described (see, e.g., Dhanasekaran S M, et al., Nature 2001; 412(6849):822-6; herein incorporated by reference in its entirety).

Example 13

Immunohistochemistry Analysis

This Example describes the prognostic utility of RKIP expression. In order to study protein expression in the 758 samples described in Example 12, standard avidin-biotin complex immunohistochemistry (IHC) was used. Briefly, antigen retrieval was performed by steaming the slides for 15 minutes in 10 mM sodium citrate buffer, pH 6.0, in a microwave oven. The slides were then incubated sequentially with primary antibody, biotinylated secondary antibody, avidin-biotin complex, and chromogenic substrate 3,3'-diaminobenzidine. RKIP protein was detected using a rabbit polyclonal anti-RKIP antibody (1:600 dilution, Upstate Biotechnology, Lake Placid, N.Y.). RKIP staining intensity was independently scored by two genitourinary pathologists blinded to Gleason score, tumor size and clinical outcome. The staining was scored as negative (1), weak (2), moderate (3), or strong (4) as previously described (see, e.g., Fu Z, et al., J Natl Cancer Inst 2003; 95(12):878-89; Perrone E E, et al., J Natl Cancer Inst 2000; 92(11):937-9; each herein incorporated by reference in their entireties). On average, four tissue cores were evaluated from each case and the median value of all measurements from a single case was used as the final score for subsequent analysis. A total of 758 samples from non-neoplastic tissue (n=57), localized PCa (n=79) and metastatic PCa (n=55) were examined.

For statistical evaluation of immunohistochemistry staining, RKIP staining was dichotomized into high (Median RKIP staining >=3) and low (median <=2) categories. The Mantel-Haenszel chi-square test was applied to compare the RKIP staining in non-neoplastic prostate, PCa, and metastases. This was followed by chi-square test for post-hoc analysis. A P value of <0.05 was considered significant. PSA recurrence was calculated from the date of surgical excision of the primary tumor to the date of recurrence or the end of follow-up. Kaplan-Meier analysis and Cox regression models were applied to evaluate the predictive values of RKIP and clinical parameters in differentiating recurrence outcome. Statistical significance in the Cox models was determined by the log-rank test.

To determine if changes in mRNA expression were reflected by protein expression, immunohistochemistry for RKIP protein expression on previously validated PCa tissue microarrays was performed (see, e.g., Rubin M A, et al., Clin Cancer Res 2000; 6(3):1038-45; Perrone E E, et al., J Natl Cancer Inst 2000; 92(11):937-9; each herein incorporated by reference in their entireties). The patient demographics for the men with primary tumors are described in detail in Table 9.

TABLE 9

CLINICAL CHARACTERISTICS OF 79 PATIENTS WHOSE RESECTED
PROSTATE CANCERS WERE EVLAUTED FOR RKIP EXPRESSION.*

| Characteristic | Total | RKIP moderate/high | RKIP negative/low | P value |
|---|---|---|---|---|
| Age (yr) | 60.3 ± 7.7 | 60.2 ± 7.4 | 60.4 ± 8.0 | 0.91† |
| Race | | | | |
| Caucasian | 52 (66) | 27 (66) | 25 (66) | 0.77# |
| African-American | 19 (24) | 9 (22) | 10 (26) | |
| Other | 8 (10) | 5 (12) | 3 (8) | |
| Length of follow-up (mo) | 50.0 ± 28.5 | 59.9 ± 22.0 | 39.3 ± 30.9 | 0.0009† |
| Pre-prostatectomy PSA (ng/mL) | 9.0 ± 8.8 | 8.7 ± 7.7 | 9.3 ± 9.9 | 0.76† |
| Maximum tumor diameter (cm) | 1.6 ± 0.7 | 1.6 ± 0.7 | 1.5 ± 0.6 | 0.40† |
| Gland weight (g) | 51.8 ± 16.6 | 53.7 ± 19.3 | 49.8 ± 13 | 0.29† |
| Gleason score - no. (%) | | | | |
| 5 | 3 (4) | 2 (5) | 1 (3) | 0.08‡ |
| 6 | 28 (35) | 19 (46) | 9 (24) | |
| DRE | | | | |
| Negative - no. (%) | 49 (62) | 27 (66) | 22 (28) | 0.47# |
| Positive - no. (%) | 30 (38) | 14 (34) | 16 (42) | |
| Pathologic stage - no. (%) | | | | |
| pT2 | 60 (76) | 35 (85) | 25 (66) | 0.04# |
| Surgical margin status | | | | |
| Negative - no. (%) | 53 (67) | 31 (76) | 22 (58) | 0.09# |
| Positive - no. (%) | 26 (33) | 10 (24) | 16 (42) | |
| PSA-defined recurrence | | | | |
| No - no. (%) | 58 (73) | 36 (88) | 22 (58) | 0.003# |
| Yes - no. (%) | 21 (27) | 5 (12) | 16 (42) | |

*Plus-minus values are means ± SD
†The P value was calculated by Wilcoxon's rank-sum test for the comparison of the RKIP moderate/high group with the RKIP negative/low group.
The P value was calculated by the student t test for the comparison of the RKIP moderate/high group with the RKIP negative/low group.
‡The P value was calculated by the Fisher's exact test for the comparison of the RKIP moderate/high group with the RKIP negative/low group.
PSA, prostate specific antigen; DRE, digital rectal examination.

Figures 9A, 9B:
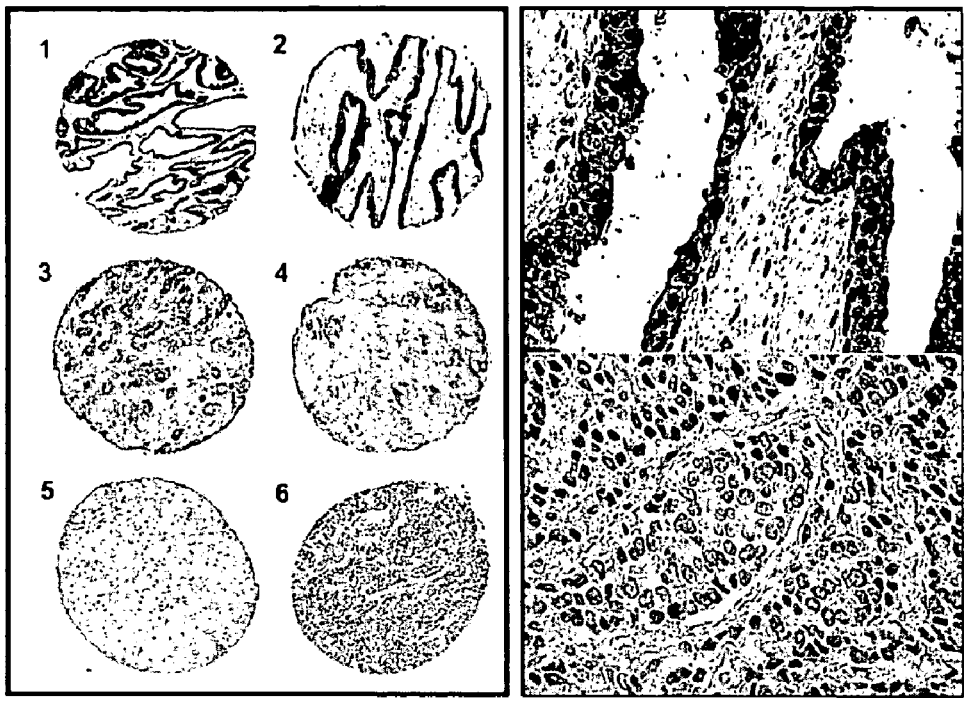
FIG. 9 shows RKIP protein is downregulated in PCa. (a) Representative elements of a tissue microarray stained with anti-RKIP antibody. Immunohistochemistry demonstrates strong staining of non-neoplastic prostate (a1), moderate staining in localized PCa (a2), and absent or weak staining of metastatic PCa (a3). Magnification ×100. (b) RKIP expression is high in the secretary luminal cells of non-neoplastic prostate (top), but absent in metastatic PCa (bottom). Magnification ×400. (c) Histogram of RKIP expression by tissue type based on tissue microarray analysis. Tumor specimens were stratified into moderate/high RKIP expression and negative/low RKIP expression. RKIP expression decreases with increasing progression ($P<0.0001$, Mantel-Haenszel chi-square test). RKIP expression differs between all pair-wise comparisons ($P<0.0001$, chi-square analysis).
Figure 9C:
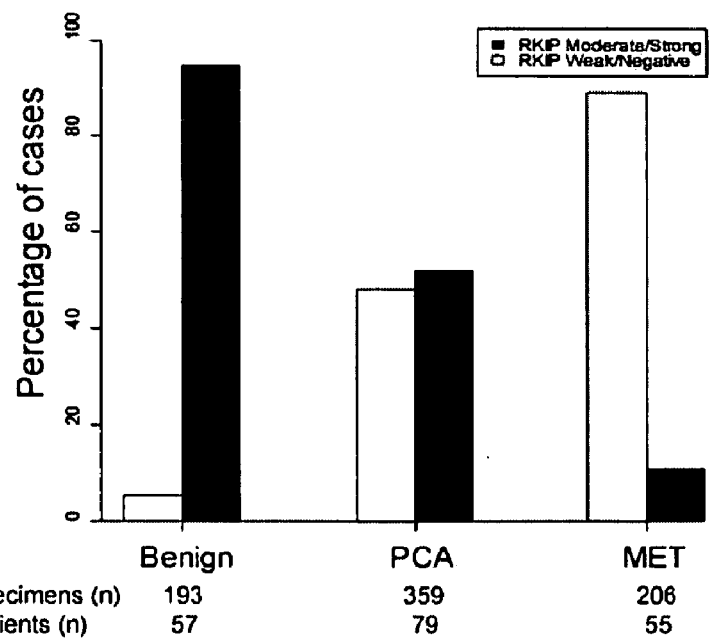

For men with metastatic cancer, pre-prostatectomy data were unavailable; however, in summary, there were 55 men with metastases with a mean age of 67 years (range: 40-84 years) approximately 36% had prostatectomy; 60% had bilateral orchiectomy; 5% had radiation therapy; and 100% had chemotherapy and hormone ablation. PCa metastases that were examined included skeletal, lymph node, hepatic, pulmonary, dural, adrenal, splenic, spine, diaphragmatic, bladder, seminal vesicle, testis, and pancreatic metastases. RKIP protein staining was cytoplasmic in all positive cases (FIGS. 9A and 9B). The prostatic origin of tumor cells expressing RKIP was confirmed by positive IHC staining for PSA. The intensity of RKIP staining was dichotomized into two groups; weak/negative staining (score of 1 or 2) and moderate/strong staining (score of 3 or 4). IHC analysis revealed that 95% of the non-neoplastic prostate samples had moderate/strong staining; whereas, only 5% had negative/weak staining (FIG. 9C). This differed from primary tumors of which 52% had moderate/strong staining and 48% had negative/weak staining. Finally, only 11% of the metastatic tumors had moderate/strong staining; whereas, 89% had negative/weak staining (FIG. 9C). These data indicate that RKIP protein expression decreases with overall PCa progression (P<0.0001, Mantel-Haenszel chi-square test). Furthermore, there was a significant decrease in RKIP staining intensity between localized PCa compared to primary tumor tissue (P<0.0001, chi-square test). Similarly, metastatic PCa had significantly lower expression of RKIP than did clinically localized PCa (P<0.0001, chi-square test). As these results show, RKIP expression indicates the aggressiveness of an individual's PCa.

This example demonstrates the prognostic utility of RKIP expression in primary tumors. In this example, the association of RKIP protein expression with clinical and pathological parameters was evaluated. The clinical and pathologic characteristics of the men with primary tumors are shown in Table 9. After a mean follow-up of 50.0 months (+28.5), 21 of the 79 patients (27%) had PSA recurrence. The 5- and 7-year disease-specific survival rates for the entire cohort of patients were 72.8% (+5.26%) and 69.6% (+5.91%), respectively. Clinical stage was dichotomized by results of the digital rectal examination (DRE) into palpable (or positive) and non-palpable (or negative) groups. Pathological stage was simplified to two classes, pT2 (organ-confined) and pT3 (extraprostatic extension and/or seminal vesicle invasion). The natural logarithm of the preoperative level of PSA (ln[PSA]) was used as previously described (see, e.g., Dhanasekaran S M, et al., Nature 2001; 412(6849):822-6; herein incorporated by reference in its entirety). RKIP expression was inversely correlated with pathological stage, length of follow-up and PSA recurrence rate (Table 9). As these results show, there was no significant correlation between RKIP expression level and Gleason score, surgical margin (SM) status, tumor size, gland weight, Ln[PSA] or clinical stage.

Figure 10A:
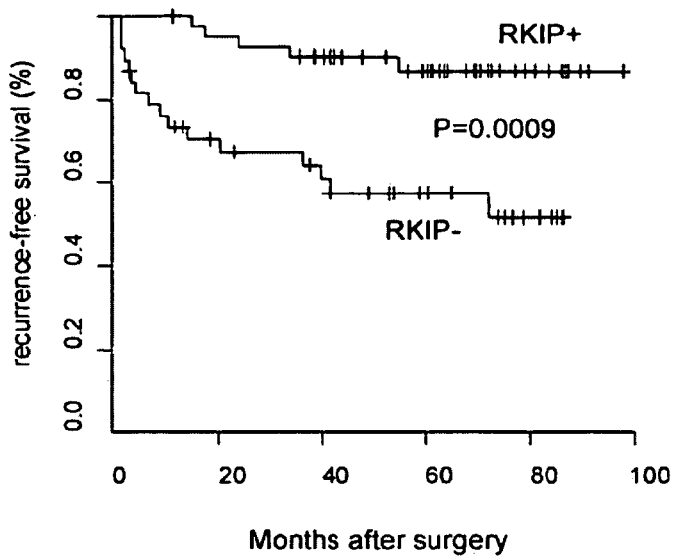
FIG. 10 shows Kaplan-Meier estimates of PSA recurrence-free probability for the patients with clinically localized PCa. (a) All patients: Patients were stratified on the basis of moderate/high (RKIP+) or negative/low (RKIP−) RKIP expression levels. P value was calculated using the log-rank test. (b) Patients with Gleason score 6 or 7 tumors: Patients were stratified on the basis of moderate/high (RKIP+) or negative/low (RKIP−) RKIP expression levels. P value was calculated using the log-rank test.

PSA failure (also termed PSA recurrence or biochemical relapse) is defined as developing elevated PSA levels greater than 0.2 ng/ml after radical prostatectomy (see, e.g., Pound CR, et al., Jama 1999; 281(17):1591-7; herein incorporated by reference in its entirety). Patients demonstrating PSA failure typically progress to development of distant metastases and death from PCa. To test whether RKIP can be used as a potential PCa biomarker to predict clinical outcome in men treated with prostatectomy for clinically localized PCa, outcome analysis on 359 prostate samples from the 79 men with localized PCa (each patient's tumor is evaluated using an average of 5 samples) was performed. Kaplan-Meier analysis (FIG. 10a) revealed that negative/weak RKIP staining predicted an earlier PSA recurrence than moderate/strong RKIP expression. At seven years of follow-up, only 13% of the patients with moderate/strong staining tumors had PSA recurrence, compared to 48% of the patients with negative/weak staining tumors (P<0.001, log rank).

To explore what clinical and pathological parameters could predict early PSA recurrence, a univariate analysis was performed (Table 10). At the univariate level, tumor diameter, pathological stage, SM status and Ln[PSA] were directly associated with PSA recurrence. In contrast, RKIP protein expression was inversely associated with PSA recurrence. Gland weight, Gleason score and clinical stage were not associated with PSA recurrence.

TABLE 10

UNIVARIATE AND MULTIVARIABLE COX HAZARDS ANALYSIS OF CLINICOPATHOLOGICAL PARAMETERS AND RKIP EXPRESSION IN 79 PATIENTS WITH PROSTATE CANCER

| Variable | Univariate analysis HR (95% CI) | P value† | Multivariate analysis HR (95% CI) | P value† |
|---|---|---|---|---|
| RKIP | 0.21 (0.08-0.58) | 0.002 | 0.11 (0.03-0.38) | 0.0005 |
| Gleason score | 1.80 (0.70-4.63) | 0.23 | 0.38 (0.12-1.20) | 0.10 |
| Maximal tumor diameter | 3.15 (1.34-7.42) | 0.009 | 1.29 (0.46-3.60) | 0.63 |
| Pathological stage | 3.70 (1.57-8.74) | 0.003 | 1.33 (0.36-4.88) | 0.66 |
| SM | 6.34 (2.54-15.80) | <0.0001 | 6.72 (2.21-20.49) | 0.0008 |
| DRE | 1.66 (0.71-3.91) | 0.25 | 1.48 (0.43-5.07) | 0.53 |
| Ln[PSA] | 2.46 (1.39-4.36) | 0.002 | 2.91 (1.33-6.37) | 0.007 |
| Gland Weight | 0.99 (0.96-1.02) | 0.45 | 1.00 (0.96-1.03) | 0.93 |

*HR = hazard ratio;
CI = confidence interval;
SM = surgical margin status;
PSA, prostate specific antigen;
Ln[PSA] = natural logarithm of the pretreatment prostate-specific antigen level (ng/mL).
†Cox regression analysis. All statistical tests were two-sided.

To examine the prognostic value of RKIP expression independent of known clinical and pathologic parameters, multivariate analysis was performed (Table 10). To fit a multivariable Cox hazards regression model, RKIP expression level along with tumor diameter, pathological stage, SM status, Ln[PSA], gland weight, Gleason score and clinical stage were included in the model. The analysis indicated that RKIP expression was the most significant predictor of PSA recurrence followed by SM status and Ln[PSA] (Table 10). As in the univariate analysis, RKIP was inversely correlated with PSA recurrence and SM status and Ln[PSA] were directly correlated with PSA recurrence. Although tumor size and pathologic stage had a strong association with PSA recurrence at the univariate level, they had no independent association with outcome at the multivariate level. A multivariate analysis of only the three independent factors revealed that RKIP maintained significance as an independent factor, giving a final best fit multivariate model predictive of PSA recurrence that included the following terms and their hazard ratios (95% CI; all at P≦0.0005, Cox regression analysis): RKIP expression, 0.15, (0.05-0.44); Ln[PSA], 6.73 (2.62-17.32) and surgical margin status 3.15 (1.68-5.88). These results indicate that patients with a negative/low RKIP expression are 85% more likely to have an early PSA recurrence compared to those with moderate/high RKIP expression. As these results show, expression of a MSG, namely RKIP, adds considerably to a prognostic model for PSA recurrence.

Figure 10B:
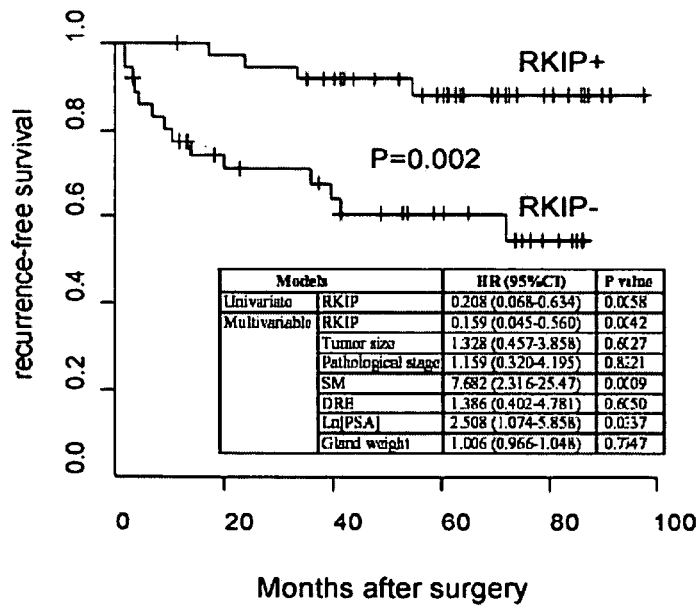

The majority of CaP patients who undergo prostatectomy have intermediate Gleason scores (i.e., scores of 6-7) (see, e.g., Ayala G, et al., Clin Cancer Res 2003; 9(13):4792-801; Ayala G, et al., Cancer Res 2003; 63(19):6244-51; each herein incorporated by reference in their entireties). These Gleason scores are fairly non-informative as it is difficult to determine prognosis of patients that have tumors with these Gleason scores (see, e.g., Ayala G, et al., Clin Cancer Res 2003; 9(13):4792-801; Ayala G, et al., Cancer Res 2003; 63(19):6244-51; Dash A, et al., American Joint Committee on Cancer. Urology 2002; 60(2):276-80; each herein incorporated by reference in their entireties). Accordingly, to determine if RKIP expression could provide additional prognostic information for this subset of patients, multivariate Cox regression analysis of patients with Gleason scores 6 or 7 using clinical and pathological parameters was performed. RKIP level is statistically a stronger marker than Ln[PSA] and as good a marker as surgical margin status (FIG. 10b). Patients with tumors with Gleason score of 6 or 7 and negative/low RKIP expression have a 79.2% greater chance of PSA recurrence than those patients with tumors that have moderate/high RKIP expression. As these results show, RKIP is a useful predictor of PSA recurrence in CaP patients with Gleason scores of 6 and 7 and provide improved prognostic information than that of the currently used Gleason score in this class of patients.

Example 14

Cell Cultures and Animals used in Experiments Indicating Induction of RKIP mRNA Expression by Androgens through the Androgen Receptor This Example describes cell cultures and animals that were used in experiments indicating induction of RKIP mRNA expression by androgens through the androgen receptor. RWPE-1 cells were maintained in the complete K-SFM medium (keratinocyte-serum free medium) (Invitrogen, Carlsbad, Calif.) which contains 50 μg/ml of BPE and 5 ng/ml EGF, plus antibiotic/antimycotic mixture (Penicillin, 100 U/ml, Streptomycin 100 μg/ml and Fungizone, 25 ug/ml). Cells were passaged upon confluence and seeded at $2 \times 10^6$ cells/T-75 flask. The cells were maintained in a humidified incubator with 5% $CO_2$ at 37° C.

Approximately 6-8 weeks average age of C57BL/6 male mice purchased from Charles River (Wilmington, Mass.) were housed and maintained. Castrations consisted of removal of the testis, fat pad, and epididymis via scrotal incision. Sham castrated mouse served as control. All procedures were performed under anesthesia. At various times after castration, at least five mouse were killed and their prostate, lung, brain, spleen, stomach, liver, and muscle were harvested, washed in cold phosphate-buffered saline (PBS) and snap-frozen in liquid nitrogen before being transferred to a −70 C freezer.

For in vitro studies, RWPE cells were plated in 6-well plates with complete K-SFM medium 24 h before treatment. For dose response experiment, RWPE cells were treated with vehicle (0.001% DMSO ) or with 0.01, 0.1, 1, 5, 50 μM DHT (dissolved in 0.001% DMSO, final concentration) for 24 h. The effect of Casodex (Zeneca) on the regulation of RKIP expression by DHT was examined by treating the cells with vehicle (0.001% DMSO) or with 20 μM casodex in the presence or absence of 5 μM DHT for 24 h. Casodex was also solubilized in DMSO (0.001%, final concentration). The effect of cycloheximide on regulation of RKIP expression by androgen was tested by treating the cells with vehicle (0.001% DMSO) or with 0.5 μg/ml cycloheximide in the presence or absence of 5 μM DHT for 24 h. Cycloheximide was also dissolved in 0001% DMSO, final concentration). Cells were, then, harvested by removing the medium, washing the cells once with PBS and suspended in 1 mL of TRIzol Reagent (Invitrogen, Carlsbad, Calif.). For in vivo studies, tissues were homogenized in 1 mL of TRIzol Reagent using a pellet pestle (kontes, Vineland, N.J.). Total RNA was isolated following the TRI Reagent protocol. RNA concentration was determined by absorbance at 260 nm using a UV spectrophotometer (Pharmacia Biotech, Uppsala, Sweden). 100 ng of total RNA was utilized for real-time reverse transcription-polymerase chain reaction (RT-PCR) using QuantiTect SYBR Green RT-PCR kit (Valencia, Calif.). RT-PCR reactions were subjected to 45 cycles of 95° C. for 15 seconds, 58° C. for 20 seconds, and 72° C. for 30 seconds. RT-PCR of β-globule as an internal control to ensure equal loading of samples. Oligonucleotide primers synthesized by invitrogen were used to amplify a 400-base pair (bp) fragment of mouse RKIP RNA (sense primer: 5'-AACAGGCCCAGCAG-CATTTCAT-3' (SEQ ID NO:5); antisense primer: 5'-ACAGCTTGGGCACATAGTCATC-3' (SEQ ID NO:6)) and a 300 bp fragment of human RKIP RNA (sense primer: 5'-AGGACAGGCCGCTAAAGTGTGAC-3' (SEQ ID NO:7); antisense primer: 5'-GTCACCCTCAACTAC-CATCTGACTG-3' (SEQ ID NO:8)). A fragment of mouse β-microglobulin RNA (sense primer: 5'-CTCGCGC-TACTCTCTTCTCTTTCTGG-3' (SEQ ID NO:9); antisense primer: 5'- GCTTACATGTCTCGATCCCACTTAA-3' (SEQ ID NO:10)) and 120 bp fragment of human β-microglobulin RNA (sense primer: 5'- ACCCCCACTGAAAAAGATGA-3' (SEQ ID NO:11); antisense primer: 5'-ATCTTCAAACCTC-CATGATG-3' (SEQ ID NO:12)) were used. Fold changes were calculated relative to DMSO control-treated samples.

Example 15

RKIP is Regulated by Androgen

Figure 11A:
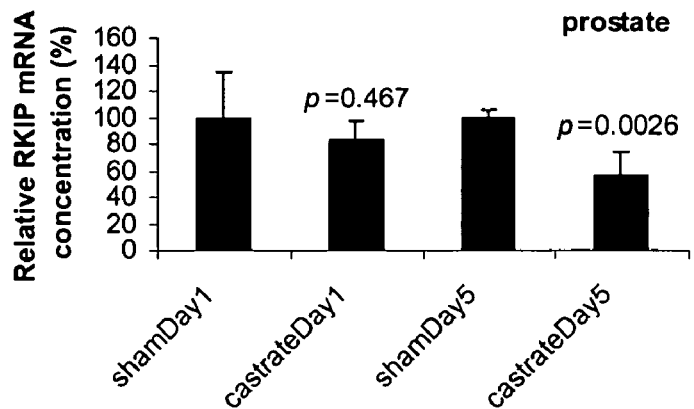
FIG. 11 shows relative RKIP mRNA concentration as a function of castration or no castration at days 1 and 5 for 11A) prostate tissue; 11B) muscle tissue; and 11C) lung tissue.
Figure 11B:
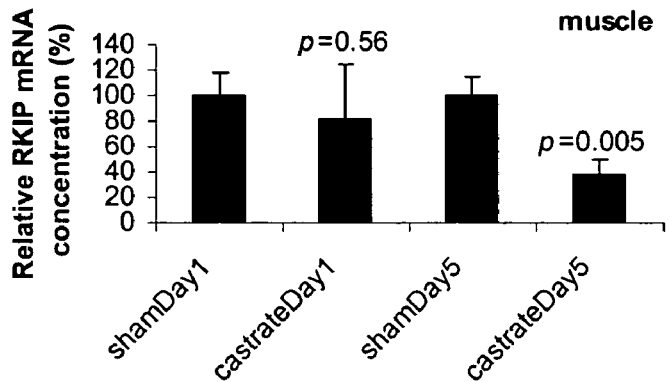
Figure 11C:
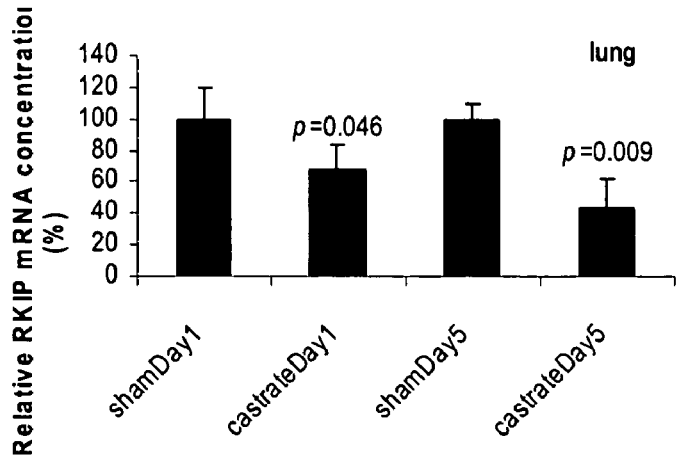

This Example describes the effect of androgen withdrawal on RKIP expression. To determine whether RKIP was regulated by androgen, 6-8 week old C57BL/6 male mice were castrated and examined RKIP expression level in response to orchidectomy. RNA was extracted from various organs previously shown to express RKIP (see, e.g., Frayne, J., et al., Cell Tissue Res, 298: 415-423, 1999; Bollengier, F. and Mahler, A. J Neurochem, 50: 1210-1214, 1988; each herein incorporated by reference in its entirety) at various time points, day 1, day 5, after castration, but prior to the onset of an atrophic state. Real-time RT-PCR analysis revealed that 24 hrs after castration, the steady-state, high levels of RKIP mRNA began decreasing in prostate tissue, and by 120 h, the level was decreased about 2-fold (FIG. 11A). These results indicate that maintenance of a high level of expression of RKIP in prostate requires testicular androgens. In addition, RKIP levels markedly decreased (2-3 fold) by day 5 after castration in muscle (FIG. 11B) and lung (FIG. 11C). As these results show, the effect of androgen withdrawal on RKIP expression level is tissue-specific.

Example 16

Ability of Androgens to Regulate the Expression of RKIP

This Example describes the ability of androgens to regulate the expression of RKIP. The mechanisms by which androgen plays a role in RKIP expression was investigated. RWPE-1 cells are non-neoplastic adult human prostatic epithelial cells from a white male donor (see, e.g., Bello, D., et al., Carcinogenesis, 18: 1215-1223, 1997; herein incorporated by reference in its entirety). RWPE cells express wild-type androgen receptor and exhibit growth and differentiation characteristics of normal prostate epithelium (see, e.g., Bello, D., et al., Carcinogenesis, 18: 1215-1223, 1997; herein incorporated by reference in its entirety). Therefore, RWPE cells provide useful cell culture models for studies on gene regulation in prostate epithelia.

Figure 12A:
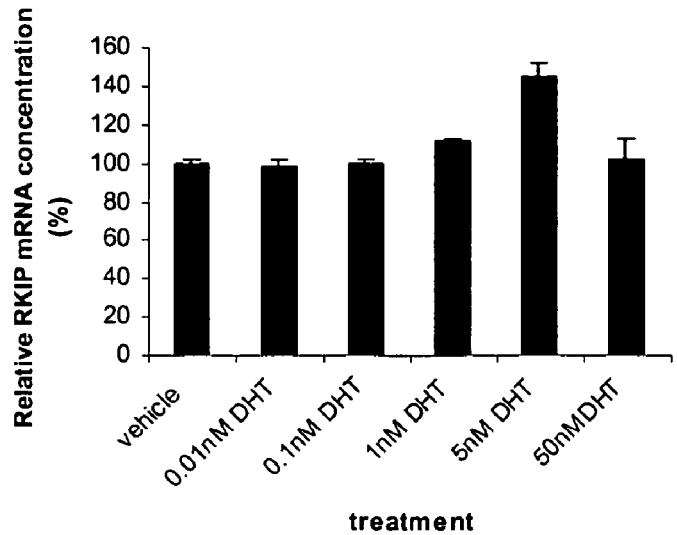
FIG. 12 shows relative RKIP mRNA concentration as a function of 12A) DHT treatment; 12B) DHT, BIC and DHT/BIC treatment; and 12C) CHX and DHT/CHX treatment.
Figure 12B:
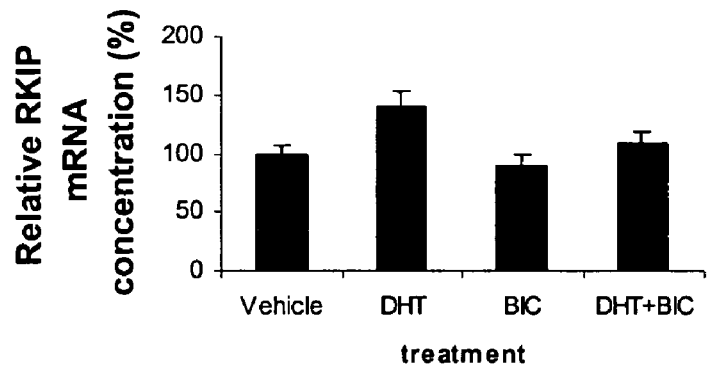

To evaluate the ability of androgens to regulate the expression of RKIP, RWPE cells were plated in 6-well plates and after 24 h these cells were treated with various concentrations of DHT, the in vivo ligand of AR. An initial experiment showed that 24 h stimulation resulted in maximal induction. The RNA was analyzed by real-time PCR for human RKIP expression. DHT caused a dose-dependent increase in the RKIP mRNA expression (FIG. 12A). A maximum induction of 1.5-fold was seen at 5 nM. After peaking at 5 nM, RKIP levels gradually decreased (FIG. 12A). A very low concentration of DHT (0.1 nM) showed almost no induction of RKIP expression. This concentration is below the $K_d$ value of DHT for the androgen receptor (approximately 0.1 nM). However, 1 nM DHT induced a significant (P<0.01) increase in RKIP mRNA. Saturating amounts of DHT (>=5 nM) produced significant (P<0.01) induction of RKIP expression. This pattern of induction followed the expected binding kinetics of DHT to the androgen receptor (e.g., Kuiper, G. G., et al., Biochem J, 296 (Pt 1): 161-167, 1993; herein incorporated by reference in its entirety). The present invention is not limited to a particular mechanism. Indeed, an understanding of the mechanism is not necessary to practice the present invention. Nonetheless, these results suggested that level of RKIP mRNA expression is induced by androgens through the androgen receptor in a concentration-dependent manner. This effect was substantially reduced by the antiandrogen Casodex (BIC) (FIG. 12B). As these results show, androgen plays a role in regulation of RKIP expression level.

Example 17

Androgen Stimulates RKIP Expression

Figure 12C:
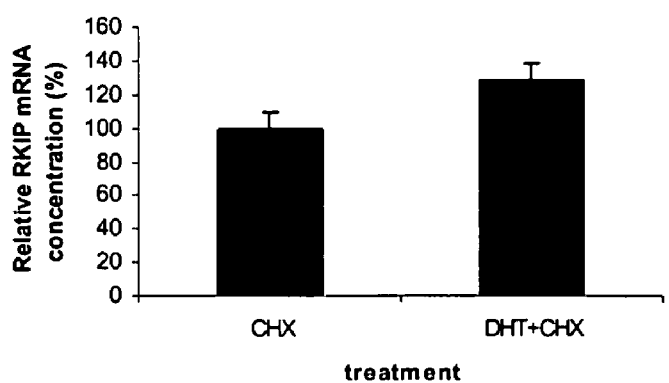

This Example describes how de novo protein synthesis is not required for the androgen induction of RKIP. Although some androgen-induced genes are regulated directly by androgen and its ligand-AR, others are regulated through indirect mechanisms by which androgens increase the expression of an unknown protein that directly induces the expression of target genes. To test whether androgen directly or indirectly stimulates RKIP expression, the treatment of 5 nM DHT for 24 h was repeated with or without the potent protein synthesis inhibitor cycloheximide (CHX). CHX treatment alone did not change the expression of RKIP (FIG. 12C). Cells treated with CHX still responded to DHT treatment with an increase in RKIP expression (FIG. 12C). This level of expression was not as high as that seen in the cells treated with DHT alone, but it was higher than control levels (P=0.04). The present invention is not limited to a particular mechanism. Indeed, an understanding of the mechanism is not necessary to practice the present invention. Nonetheless, these results are due to the highly toxic effects of CHX on cells. As these results show, de novo protein synthesis is not required for the androgen induction of RKIP.

Example 18

Effect of Androgen on RKIP Promoter Activity

This Example describes the effect of androgen on the RKIP promoter. To examine the effect of androgen on the RKIP promoter activity, RWPE cells were transfected with luciferase reporter plasmid containing a human RKIP promoter fragment from −2206 to −26 bp.

RWPE cells (50,000 cells/well) were plated in a 12-well plate with complete K-SFM medium 24 h before transfection. These cells were transfected with 0.4 ug of both luciferase reporter plasmid containing a RKIP promoter fragment and a reporter plasmid (pRL-TK, promega, Madison, Wis.) per well using Lipofectamine Plus reagent (Invitrogen, Carlsbad, Calif.) according to manufacturer's guidelines. 24 h after transfection, cells were washed and fed with fresh medium with 0.001% DMSO or with DHT (dihydrotesterone; 5 nM, 10 nM), and the incubations were continued for an additional 24 h. For luciferase assays, cells were harvested by removing the medium, washing the cells once with PBS, and incubating with 100 ul passive buffer (Promega, Madison, Wis.) for 1 h at room temperature. Both firefly and *Renilla* LUC activity were determined in a lumicounter (LUM/star, BMG Lab Technologies, Inc., Durham, N.C.) using the dual-luciferase reporter assay system (Promega, Madison, Wis.). Fold changes were calculated relative to DMSO control-treated samples. All experiments were performed in triplicate.

Figure 13:
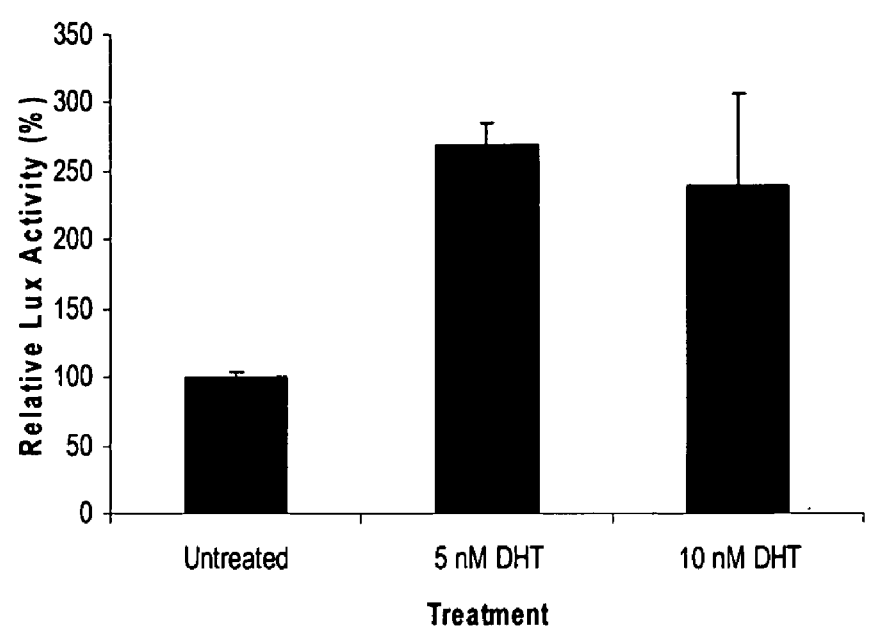
FIG. 13 shows relative luciferase activity for RWPE cells transfected with luciferase reporter plasmid containing a human RKIP promoter fragment in the presence of no treatment, 5 nM DHT treatment and 10 nM DHT treatment.

About 24 h after transfection, the cells were washed and fed with fresh medium with 0.001% DMSO or with DHT (dihydrotesterone; 5 nM, 10 nM), and incubations were continued for an additional 24 h. When compared to basal activity, the plasmid containing the RKIP promoter region exhibited an approximately 3-fold increase in luciferase activity upon the addition of the androgen analogue DHT (FIG. 13). As these results show, androgens regulate RKIP promoter activity and thus transcription.

Examination of human RKIP promoter region revealed the presence of one putative androgen-response element (ARE) (see, e.g., Kousteni, S., et al., Cell, 104: 719-730, 2001; herein incorporated by reference in its entirety). A 15-bp sequence (5'-TGTCCAggaTGGTCT-3') with significant homology (80%) to the consensus ARE, 5'-GGA/TACAnnnTGTTCT-3' (see, e.g., Roche, P. J., et al., Mol Endocrinol, 6: 2229-2235, 1992; herein incorporated by reference in its entirety), is located at position −569, relative to the putative transcriptional start site. These results indicate that this 15-bp sequence may be responsible for androgen induction of RKIP transcription.

Possible interaction of AR from RWPE nuclear extracts with a radiolabeled putative RKIP ARE probe was also assessed by EMSA. Nuclear extracts from RWPE were prepared and used for EMSA as previously described (see, e.g., Simeone, D. M., et al., Am J Physiol Cell Physiol, 281: C311-319, 2001; herein incorporated by reference in its entirety). Nuclear extracts were prepared from cells treated with vehicle (0.1% ethanol), 5 nM DHT for 30 sec, 1 h, or 2 h before harvesting. EMSA was carried out using a gel shift assay system (Promega, Madison, Wis.). Nuclear protein (10 µg) was incubated with gel shift binding buffer [10 mM HEPES, 10% glycerol, 1 mM dithiothreitol, 1 mg of poly(dI-dC) per 10 ml, and 5 mg of BSA per 10 ml] and a putative ARE consensus oligonucleotide probe labeled with [γ-32P] ATP by T4 polynucleotide kinase. The putative ARE consensus oligonucleotides having sequences (5'-CCTTGTCCAG-GATGGTCTCAAAC-3' (SEQ ID NO:13)) corresponding to the region between −2206 to −26 bp of the RKIP promoter were synthesized by invitrogen (Carlsbad, Calif.) and used as probe. The reaction was allowed to proceed for 30 min at room temperature. For cold competition experiments, the extract was preincubated for 30 min with 10-, 20-, or 100-fold molar excess of unlabeled oligonucleotide. For the antibody supershift assay, 1 µg of anti-AR antibody (PG-21, Upstate, Lake Placid, N.Y.) was incubated with the nuclear extracts for 30 min at room temperature prior to the addition of labeled probe. DNA-protein complexes were separated under nondenaturing condition in a 6% polyacrylamide gel (29:1) containing 2.5% glycerol. Gels were transferred to Whatman paper on a gel dryer, exposed to a Bio-Rad GS-250 screen overnight, and then analyzed on a Bio-Rad molecular imager. Bands form dried EMSA gels were quantified by the STORM 860 PhosphorImager (Molecular Dynamics).

Figure 14:
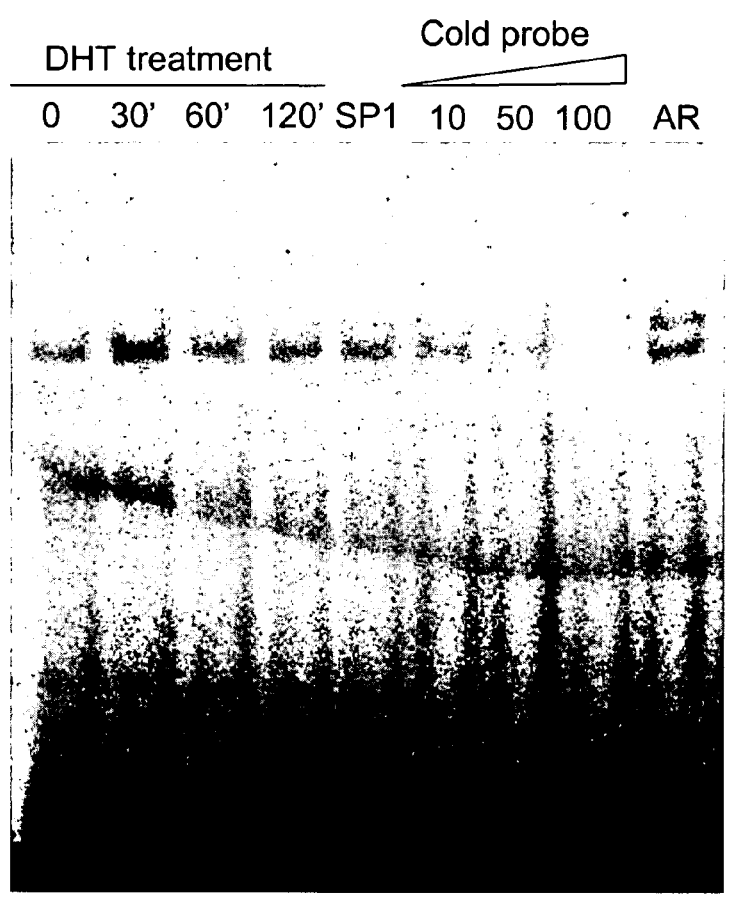
FIG. 14 shows androgen receptor specific binding to the RKIP promoter.

Assessment by EMSA for possible interaction of AR from RWPE nuclear extracts with a radiolabeled putative RKIP ARE probe revealed a low-mobility complex. A rapid increase in DNA binding activity was detected as early as 30 min following DHT treatment. Specificity of AR protein binding to the RKIP ARE was confirmed using three different approaches. These included supershift of the protein/DNA complex with an antibody to the AR DNA binding domain (FIG. 14, lane 9), and by competition experiments using 100-fold excess unlabeled putative RKIP ARE oligonucleotide (specific competitor; FIG. 14, lane 8)) and SP1 oligonucleotide (nonspecific competitor; FIG. 14, lane 5)). As these results show, AR binds to RKIP promoter.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for predicting prostate cancer recurrence, comprising:
    a) providing a resected or biopsied prostate tissue sample from a subject diagnosed with prostate cancer and a resected or biopsied prostate tissue sample from a control-subject diagnosed with non-metastatic prostate cancer,
    b) determining the amount of RKIP protein in said prostate tissue sample from said subject and from said control subject,
    c) comparing said determined amount of RKIP protein in said prostate tissue sample from said subject and said control-subject, and
    d) providing a prognosis to said subject regarding risk of prostate cancer recurrence after treatment for prostate cancer based upon said comparing of RKIP protein amount in said prostate tissue sample from said subject and from said control-subject, wherein said subject has a higher likelihood of prostate cancer recurrence after treatment for prostate cancer if said subject's determined RKIP protein amount is less than said control-subject's determined RKIP protein amount.

2. The method of claim 1, wherein said prostate tissue sample is a prostate tissue tumor sample.

3. The method of claim 1, wherein said detecting the presence or absence of RKIP protein comprises exposing said prostate tissue sample to an antibody that specifically binds to RKIP protein and detecting the binding of said antibody to said RKIP protein.

4. The method of claim 2, wherein said prostate tissue tumor sample comprises prostate primary tumor tissue.

5. The method of claim 2, wherein said prostate tissue tumor sample comprises metastatic prostate tumor tissue.

* * * * *

SEQUENCE LISTING

<160> NUMBER OF SEQ ID NOS: 13

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
caatgacatc agcagtggca cagtc                                          25

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
cacatagtca tcccactcgg cctg                                           24

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
tgaaggtcgg tgtgaacgga tttggtc                                        27

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
catgtaggcc atgaggtcca ccac                                           24

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
aacaggccca gcagcatttc at                                             22

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
acagcttggg cacatagtca tc                                             22

<210> SEQ ID NO 7
<211> LENGTH: 23

```
<212> TYPE: DNA
<213> ORGANISM: Artificial Sequence
<220> FEATURE:
<223> OTHER INFORMATION: Synthetic

<400> SEQUENCE: 7
aggacaggcc gctaaagtgt gac                                              23

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
gtcaccctca actaccatct gactg                                            25

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
ctcgcgctac tctcttctct ttctgg                                           26

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
gcttacatgt ctcgatccca cttaa                                            25

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11 accccactg aaaaagatga                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
atcttcaaac ctccatgatg                                                  20

<210> SEQ ID NO 13
<211> LENGTH: 23
<212> TYPE: DNA
<213> ORGANISM: Artificial Sequence
```

-continued

```
<220> FEATURE:
<223> OTHER INFORMATION: Synthetic

<400> SEQUENCE: 13
ccttgtccag gatggtctca aac                                              23
```